(12) United States Patent
Hudson et al.

(10) Patent No.: US 6,689,746 B2
(45) Date of Patent: *Feb. 10, 2004

(54) USE OF ISOLATED DOMAINS OF TYPE IV COLLAGEN TO MODIFY CELL AND TISSUE INTERACTIONS

(75) Inventors: Billy G. Hudson, Lenexa, KS (US); Michael P. Sarras, Jr., Kansas City, KS (US)

(73) Assignee: Kansas University Medical Center, Kansas City, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/134,899

(22) Filed: Apr. 29, 2002

(65) Prior Publication Data

US 2003/0017968 A1 Jan. 23, 2003

Related U.S. Application Data

(63) Continuation of application No. 09/277,665, filed on Mar. 26, 1999, now Pat. No. 6,440,729, and a continuation-in-part of application No. 09/183,548, filed on Oct. 30, 1998, now Pat. No. 6,384,012, which is a continuation of application No. 08/800,965, filed on Feb. 18, 1997, now Pat. No. 5,856,184, which is a continuation of application No. 08/497,206, filed on Jun. 30, 1995, now Pat. No. 5,691,182.

(60) Provisional application No. 60/106,170, filed on Oct. 29, 1998, and provisional application No. 60/079,783, filed on Mar. 27, 1998.

(51) Int. Cl.$^7$ .................................................. C12N 5/00
(52) U.S. Cl. ............................ 514/2; 435/325; 530/324; 530/350; 530/353; 530/356
(58) Field of Search ......................... 435/325; 530/324, 530/350, 353, 356; 514/2

(56) References Cited

U.S. PATENT DOCUMENTS

| | | | |
|---|---|---|---|
| 5,567,609 A | * | 10/1996 | Sarras, Jr. et al. |
| 5,691,182 A | * | 11/1997 | Sarras, Jr. et al. |
| 5,856,184 A | * | 1/1999 | Sarras, Jr. et al. |
| 6,384,012 B1 | * | 5/2002 | Sarras, Jr. et al. |
| 6,440,729 B1 | * | 8/2002 | Hudson et al. |

* cited by examiner

*Primary Examiner*—Leon B. Lankford, Jr.
(74) *Attorney, Agent, or Firm*—McDonnell Boehnen Hulbert & Berghoff

(57) ABSTRACT

The instant invention provides methods and kits for inhibiting angiogenesis, tumor growth and metastasis, and endothelial cell interactions with the extracellular matrix, involving contacting the tumor or animal tissue with at least one isolated type IV collagen NC1 α chain monomer. In a specific embodiment of the invention, the isolated domain of type IV collagen comprises the NC1 (α1), (α2), (α3), or (α6) chain monomer, or protein constructs having substantially the same structure as the NC1 (α1), (α2), (α3), or (α6) chain monomer.

3 Claims, 28 Drawing Sheets

CONTROL

7S DOMAIN (50μg/ml)

NC1 DOMAIN (50μg/ml)

A. α1(IV)NC1

```
        900       910       920       930       940       950
         |         |         |         |         |         |
        CTGCCGCCTGCCTGCCTGCCACTGAGGGTTCCCAGCACCATGAGGGCCTGGATCTTCTTT
                                                   M   R   A   W   I   F   F 960       970       980       990      1000      1010
         |         |         |         |         |         |
        CTCCTTTGCCTGGCCGGGAGGGCTCTGGCAGCCCCACTAGCCGACTACAAGGACGACGAT
          L   L   C   L   A   G   R   A   L   A   A   P   L   A   D   Y   K   D   D   D 1020      1030      1040      1050      1060      1070
         |         |         |         |         |         |
        GACAAGCTAGCATCTGTTGATCACGGCTTCCTTGTGACCAGGCATAGTCAAACAATAGAT
          D   K   L   A   S   V   D   H   G   F   L   V   T   R   H   S   Q   T   I   D 1080      1090      1100      1110      1120      1130
         |         |         |         |         |         |
        GACCCACAGTGTCCTTCTGGGACCAAAATTCTTTACCACGGGTACTCTTTGCTCTACGTG
          D   P   Q   C   P   S   G   T   K   I   L   Y   H   G   Y   S   L   L   Y   V 1140      1150      1160      1170      1180      1190
         |         |         |         |         |         |
        CAAGGCAATGAACGGGCCCATGGCCAGGACTTGGGCACGGCCGGCAGCTGCCTGCGCAAG
          Q   G   N   E   R   A   H   G   Q   D   L   G   T   A   G   S   C   L   R   K 1200      1210      1220      1230      1240      1250
         |         |         |         |         |         |
        TTCAGCACAATGCCCTTCCTGTTCTGCAATATTAACAACGTGTGCAACTTTGCATCACGA
          F   S   T   M   P   F   L   F   C   N   I   N   N   V   C   N   F   A   S   R 1260      1270      1280      1290      1300      1310
         |         |         |         |         |         |
        AATGACTACTCGTACTGGCTGTCCACCCCTGAGCCCATGCCCATGTCAATGGCACCCATC
          N   D   Y   S   Y   W   L   S   T   P   E   P   M   P   M   S   M   A   P   I 1320      1330      1340      1350      1360      1370
         |         |         |         |         |         |
        ACGGGGGAAAACATAAGACCATTTATTAGTAGGTGTGCTGTGTGTGAGGCGCCTGCCATG
          T   G   E   N   I   R   P   F   I   S   R   C   A   V   C   E   A   P   A   M 1380      1390      1400      1410      1420      1430
         |         |         |         |         |         |
        GTGATGGCCGTGCACAGCCAGACCATTCAGATCCCACCGTGCCCCAGCGGGTGGTCCTCG
          V   M   A   V   H   S   Q   T   I   Q   I   P   P   C   P   S   G   W   S   S 1440      1450      1460      1470      1480      1490
         |         |         |         |         |         |
        CTGTGGATCGGCTACTCTTTTGTGATGCACACCAGCGCTGGTGCAGAAGGCTCTGGCCAA
          L   W   I   G   Y   S   F   V   M   H   T   S   A   G   A   E   G   S   G   Q 1500      1510      1520      1530      1540      1550
         |         |         |         |         |         |
        GCCCTGGCGTCCCCCGGCTCCTGCCTGGAGGAGTTTAGAAGTGCGCCATTCATCGAGTGT
```

FIG. 17a

```
                A  L  A  S  P  G  S  C  L  E  E  F  R  S  A  P  F  I  E  C
      1560       1570      1580      1590      1600      1610
       |          |         |         |         |         |
      CACGGCCGTGGGACCTGCAATTACTACGCAAACGCTTACAGCTTTTGGCTCGCCACCATA
        H  G  R  G  T  C  N  Y  Y  A  N  A  Y  S  F  W  L  A  T  I 1620       1630      1640      1650      1660      1670
       |          |         |         |         |         |
      GAGAGGAGCGAGATGTTCAAGAAGCCTACGCCGTCCACCTTGAAGGCAGGGGAGCTGCGC
        E  R  S  E  M  F  K  K  P  T  P  S  T  L  K  A  G  E  L  R 1680       1690      1700      1710      1720      1730
       |          |         |         |         |         |
      ACGCACGTCAGCCGCTGCCAAGTCTGTATGAGAAGAACATAATGAAGCCTGACTCAGCTA
        T  H  V  S  R  C  Q  V  C  M  R  R  T  -  -

1740       1750      1760      1770      1780      1790
       |          |         |         |         |         |
      CCGCGGGCCCTATTCTATAGTGTCACCTAAATGCTAGAGCTCGCTGATCAGCCTCGACTG
```

```
         900       910       920       930       940       950
          |         |         |         |         |         |
         CTGCCGCCTGCCTGCCTGCCACTGAGGGTTCCCAGCACCATGAGGGCCTGGATCTTCTTT
                                                   M   R   A   W   I   F   F 960       970       980       990      1000      1010
          |         |         |         |         |         |
         CTCCTTTGCCTGGCCGGGAGGGCTCTGGCAGCCCCACTAGCCGACTACAAGGACGACGAT
          L   L   C   L   A   G   R   A   L   A   A   P   L   A   D   Y   K   D   D   D 1020      1030      1040      1050      1060      1070
          |         |         |         |         |         |
         GACAAGCTAGCCGTCAGCATCGGCTACCTCCTGGTGAAGCACAGCCAGACGGACCAGGAG
          D   K   L   A   V   S   I   G   Y   L   L   V   K   H   S   Q   T   D   Q   E 1080      1090      1100      1110      1120      1130
          |         |         |         |         |         |
         CCCATGTGCCCGGTGGGCATGAACAAACTCTGGAGTGGATACAGCCTGCTGTACTTCGAG
          P   M   C   P   V   G   M   N   K   L   W   S   G   Y   S   L   L   Y   F   E 1140      1150      1160      1170      1180      1190
          |         |         |         |         |         |
         GGCCAGGAGAAGGCGCACAACCAGGACCTGGGGCTGGCGGGCTCCTGCCTGGCGCGGTTC
          G   Q   E   K   A   H   N   Q   D   L   G   L   A   G   S   C   L   A   R   F 1200      1210      1220      1230      1240      1250
          |         |         |         |         |         |
         AGCACCATGCCCTTCCTGTACTGCAACCCTGGTGATGTCTGCTACTATGCCAGCCGGAAC
          S   T   M   P   F   L   Y   C   N   P   G   D   V   C   Y   Y   A   S   R   N 1260      1270      1280      1290      1300      1310
          |         |         |         |         |         |
         GACAAGTCCTACTGGCTCTCTACCACTGCGCCGCTGCCCATGATGCCCGTGGCCGAGGAC
          D   K   S   Y   W   L   S   T   T   A   P   L   P   M   M   P   V   A   E   D 1320      1330      1340      1350      1360      1370
          |         |         |         |         |         |
         GAGATCAAGCCCTACATCAGCCGCTGTTCTGTGTGTGAGGCCCCGGCCATCGCCATCGCG
          E   I   K   P   Y   I   S   R   C   S   V   C   E   A   P   A   I   A   I   A 1380      1390      1400      1410      1420      1430
          |         |         |         |         |         |
         GTCCACAGTCAGGATGTCTCCATCCCACACTGCCCAGCTGGGTGGCGGAGTTTGTGGATC
          V   H   S   Q   D   V   S   I   P   H   C   P   A   G   W   R   S   L   W   I 1440      1450      1460      1470      1480      1490
          |         |         |         |         |         |
         GGATATTCCTTCCTCATGCACACGGCGGCGGGAGACGAAGGCGGTGGCCAATCACTGGTG
          G   Y   S   F   L   M   H   T   A   A   G   D   E   G   G   G   Q   S   L   V 1500      1510      1520      1530      1540      1550
```

FIG. 17b

```
         |         |         |         |         |         |
      TCACCGGGCAGCTGTCTAGAGGACTTCCGCGCCACACCATTCATCGAATGCAATGGAGGC
        S  P  G  S  C  L  E  D  F  R  A  T  P  F  I  E  C  N  G  G 1560      1570      1580      1590      1600      1610
      |         |         |         |         |         |
      CGCGGCACCTGCCACTACTACGCCAACAAGTACAGCTTCTGGCTGACCACCATTCCCGAG
        R  G  T  C  H  Y  Y  A  N  K  Y  S  F  W  L  T  T  I  P  E 1620      1630      1640      1650      1660      1670
      |         |         |         |         |         |
      CAGAGCTTCCAGGGCTCGCCCTCCGCCGACACGCTCAAGGCCGGCCTCATCCGCACACAC
        Q  S  F  Q  G  S  P  S  A  D  T  L  K  A  G  L  I  R  T  H 1680      1690      1700      1710      1720      1730
      |         |         |         |         |         |
      ATCAGCCGCTGCCAGGTGTGCATGAAGAACCTGTGAGCCGGCGCGTGCCAGGGCCCTATT
        I  S  R  C  Q  V  C  M  K  N  L  -

1740      1750      1760      1770      1780      1790
      |         |         |         |         |         |
      CTATAGTGTCACCTAAATGCTAGAGCTCGCTGATCAGCCTCGACTGTGCCTTCTAGTTGC
```

FIG. 17b c. α3(IV)NC1

```
         900       910       920       930       940       950
          |         |         |         |         |         |
         CTGCCGCCTGCCTGCCTGCCACTGAGGGTTCCCAGCACCATGAGGGCCTGGATCTTCTTT
                                                     M  R  A  W  I  F  F 960       970       980       990      1000      1010
          |         |         |         |         |         |
         CTCCTTTGCCTGGCCGGGAGGGCTCTGGCAGCCCCGCTAGCCGACTACAAGGACGACGAT
          L  L  C  L  A  G  R  A  L  A  A  P  L  A  D  Y  K  D  D  D 1020      1030      1040      1050      1060      1070
          |         |         |         |         |         |
         GACAAACGTGGAGACAGTGGATCACCTGCAACCTGGACAACGAGAGGCTTTGTCTTCACC
          D  K  R  G  D  S  G  S  P  A  T  W  T  T  R  G  F  V  F  T 1080      1090      1100      1110      1120      1130
          |         |         |         |         |         |
         CGACACAGTCAAACCACAGCAATTCCTTCATGTCCAGAGGGGACAGTGCCACTCTACAGT
          R  H  S  Q  T  T  A  I  P  S  C  P  E  G  T  V  P  L  Y  S 1140      1150      1160      1170      1180      1190
          |         |         |         |         |         |
         GGGTTTTCTTTTCTTTTTGTACAAGGAAATCAACGAGCCCACGGACAAGACCTTGGAACT
          G  F  S  F  L  F  V  Q  G  N  Q  R  A  H  G  Q  D  L  G  T 1200      1210      1220      1230      1240      1250
          |         |         |         |         |         |
         CTTGGCAGCTGCCTGCAGCGATTTACCACAATGCCATTCTTATTCTGCAATGTCAATGAT
          L  G  S  C  L  Q  R  F  T  T  M  P  F  L  F  C  N  V  N  D 1260      1270      1280      1290      1300      1310
          |         |         |         |         |         |
         GTATGTAATTTTGCATCTCGAAATGATTATTCATACTGGCTGTCAACACCAGCTCTGATG
          V  C  N  F  A  S  R  N  D  Y  S  Y  W  L  S  T  P  A  L  M 1320      1330      1340      1350      1360      1370
          |         |         |         |         |         |
         CCAATGAACATGGCTCCCATTACTGGCAGAGCCCTTGAGCCTTATATAAGCAGATGCACT
          P  M  N  M  A  P  I  T  G  R  A  L  E  P  Y  I  S  R  C  T 1380      1390      1400      1410      1420      1430
          |         |         |         |         |         |
         GTTTGTGAAGGTCCTGCGATCGCCATAGCCGTTCACAGCCAAACCACTGACATTCCTCCA
          V  C  E  G  P  A  I  A  I  A  V  H  S  Q  T  T  D  I  P  P 1440      1450      1460      1470      1480      1490
          |         |         |         |         |         |
         TGTCCTCACGGCTGGATTTCTCTCTGGAAAGGATTTTCATTCATCATGTTCACAAGTGCA
          C  P  H  G  W  I  S  L  W  K  G  F  S  F  I  M  F  T  S  A 1500      1510      1520      1530      1540      1550
```

FIG. 17c

```
         |         |         |         |         |         |
      GGTTCTGAGGGCGCCGGGCAAGCACTGGCCTCCCCCGGCTCCTGCCTGGAAGAATTCCGA
        G  S  E  G  A  G  Q  A  L  A  S  P  G  S  C  L  E  E  F  R 1560      1570      1580      1590      1600      1610
     |         |         |         |         |         |
      GCCAGCCCATTTCTAGAATGTCATGGAAGAGGAACGTGCAACTACTATTCAAATTCCTAC
        A  S  P  F  L  E  C  H  G  R  G  T  C  N  Y  Y  S  N  S  Y 1620      1630      1640      1650      1660      1670
     |         |         |         |         |         |
      AGTTTCTGGCTGGCTTCATTAAACCCAGAAAGAATGTTCAGAAAGCCTATTCCATCAACT
        S  F  W  L  A  S  L  N  P  E  R  M  F  R  K  P  I  P  S  T 1680      1690      1700      1710      1720      1730
     |         |         |         |         |         |
      GTGAAAGCTGGGGAATTAGAAAAAATAATAAGTCGCTGTCAGGTGTGCATGAAGAAAAGA
        V  K  A  G  E  L  E  K  I  I  S  R  C  Q  V  C  M  K  K  R 1740      1750      1760      1770      1780      1790
     |         |         |         |         |         |
      CACTGAGGGCCCTATTCTATAGTGTCACCTAAATGCTAGAGCTCGCTGATCAGCCTCGAC
        H  -
```

```
          900       910       920       930       940       950
           |         |         |         |         |         |
          CTGCCGCCTGCCTGCCTGCCACTGAGGGTTCCCAGCACCATGAGGGCCTGGATCTTCTTT
                                                   M  R  A  W  I  F  F 960       970       980       990      1000      1010
           |         |         |         |         |         |
          CTCCTTTGCCTGGCCGGGAGGGCTCTGGCAGCCCCGCTAGCCGACTACAAGGACGACGAT
           L  L  C  L  A  G  R  A  L  A  A  P  L  A  D  Y  K  D  D  D 1020      1030      1040      1050      1060      1070
           |         |         |         |         |         |
          GACAAGCCTGGATACCTCGGTGGCTTCCTCCTGGTTCTCCACAGTCAGACGGACCAGGAG
           D  K  P  G  Y  L  G  G  F  L  L  V  L  H  S  Q  T  D  Q  E 1080      1090      1100      1110      1120      1130
           |         |         |         |         |         |
          CCCACCTGCCCCCTGGGCATGCCCAGGCTCTGGACTGGGTATAGTCTGTTATACCTGGAA
           P  T  C  P  L  G  M  P  R  L  W  T  G  Y  S  L  L  Y  L  E 1140      1150      1160      1170      1180      1190
           |         |         |         |         |         |
          GGGCAAGAGAAAGCTCACAATCAAGACCTTGGTCTGGCAGGGTCTTGCCTTCCCGTATTT
           G  Q  E  K  A  H  N  Q  D  L  G  L  A  G  S  C  L  P  V  F 1200      1210      1220      1230      1240      1250
           |         |         |         |         |         |
          AGCACGCTGCCCTTTGCCTACTGCAACATCCACCAGGTGTGCCACTATGCCCAGAGAAAC
           S  T  L  P  F  A  Y  C  N  I  H  Q  V  C  H  Y  A  Q  R  N 1260      1270      1280      1290      1300      1310
           |         |         |         |         |         |
          GACAGATCCTACTGGCTGGCCAGCGCTGCGCCCCTCCCCATGATGCCACTCTCTGAAGAG
           D  R  S  Y  W  L  A  S  A  A  P  L  P  M  M  P  L  S  E  E 1320      1330      1340      1350      1360      1370
           |         |         |         |         |         |
          GCGATCCGCCCCTATGTCAGCCGCTGTGCGGTATGCGAGGCCCCGGCCCAGGCGGTGGCG
           A  I  R  P  Y  V  S  R  C  A  V  C  E  A  P  A  Q  A  V  A 1380      1390      1400      1410      1420      1430
           |         |         |         |         |         |
          GTGCACAGCCAGGACCAGTCCATCCCCCCATGTCCGCAGACCTGGAGGAGCCTCTGGATC
           V  H  S  Q  D  Q  S  I  P  P  C  P  Q  T  W  R  S  L  W  I 1440      1450      1460      1470      1480      1490
           |         |         |         |         |         |
          GGGTATTCATTCCTGATGCACACAGGAGCTGGGGACCAAGGAGGAGGGCAGGCCCTTATG
           G  Y  S  F  L  M  H  T  G  A  G  D  Q  G  G  G  Q  A  L  M 1500      1510      1520      1530      1540      1550
```

FIG. 17d

```
       |         |         |         |         |         |
TCACCTGGCAGCTGCCTGGAAGATTTCAGAGCAGCACCATTCCTTGAATGCCAGGGCCGG
   S  P  G  S  C  L  E  D  F  R  A  A  P  F  L  E  C  Q  G  R 1560      1570      1580      1590      1600      1610
   |         |         |         |         |         |
CAGGGAACTTGCCACTTTTTCGCAAATAAGTATAGCTTCTGGCTCACAACGGTGAAAGCA
 Q  G  T  C  H  F  F  A  N  K  Y  S  F  W  L  T  T  V  K  A 1620      1630      1640      1650      1660      1670
   |         |         |         |         |         |
GACTTGCAGTTTTCCTCTGCTCCAGCACCAGACACCTTAAAAGAAAGCCAGGCCCAACGC
 D  L  Q  F  S  S  A  P  A  P  D  T  L  K  E  S  Q  A  Q  R 1680      1690      1700      1710      1720      1730
   |         |         |         |         |         |
CAGAAAATCAGCCGGTGCCAGGTCTGCGTGAAGTATAGCTAGGGGCCCTATTCTATAGTG
 Q  K  I  S  R  C  Q  V  C  V  K  Y  S  -

1740      1750      1760      1770      1780      1790
   |         |         |         |         |         |
   TCACCTAAATGCTAGAGCTCGCTGATCAGCCTCGACTGTGCCTTCTAGTTGCCAGCCATC
```

```
        900       910       920       930       940       950
         |         |         |         |         |         |
        CTGCCGCCTGCCTGCCTGCCACTGAGGGTTCCCAGCACCATGAGGGCCTGGATCTTCTTT
                                                  M  R  A  W  I  F  F 960       970       980       990      1000      1010
         |         |         |         |         |         |
        CTCCTTTGCCTGGCCGGGAGGGCTCTGGCAGCCCCGCTAGCTGACTACAAGGACGACGAT
         L  L  C  L  A  G  R  A  L  A  A  P  L  A  D  Y  K  D  D  D 1020      1030      1040      1050      1060      1070
         |         |         |         |         |         |
        GACAAAGGTCCCCCTGGAACCTCCTCTGTTGCACATGGATTTCTTATTACACGCCACAGC
         D  K  G  P  P  G  T  S  S  V  A  H  G  F  L  I  T  R  H  S 1080      1090      1100      1110      1120      1130
         |         |         |         |         |         |
        CAGACAACGGATGCACCACAATGCCCACAGGGAACACTTCAGGTCTATGAAGGCTTTTCT
         Q  T  T  D  A  P  Q  C  P  Q  G  T  L  Q  V  Y  E  G  F  S 1140      1150      1160      1170      1180      1190
         |         |         |         |         |         |
        CTCCTGTATGTACAAGGAAATAAAAGAGCCCACGGTCAAGACTTGGGGACGGCTGGCAGC
         L  L  Y  V  Q  G  N  K  R  A  H  G  Q  D  L  G  T  A  G  S 1200      1210      1220      1230      1240      1250
         |         |         |         |         |         |
        TGCCTTCGTCGCTTTAGTACCATGCCTTTCATGTTCTGCAACATCAATAATGTTTGCAAC
         C  L  R  R  F  S  T  M  P  F  M  F  C  N  I  N  N  V  C  N 1260      1270      1280      1290      1300      1310
         |         |         |         |         |         |
        TTTGCTTCAAGAAATGACTATTCTTACTGGCTCTCTACCCCAGAGCCCATGCCAATGAGC
         F  A  S  R  N  D  Y  S  Y  W  L  S  T  P  E  P  M  P  M  S 1320      1330      1340      1350      1360      1370
         |         |         |         |         |         |
        ATGCAACCCCTAAAGGGCCAGAGCATCCAGCCATTCATTAGTCGATGTGCAGTATGTGAA
         M  Q  P  L  K  G  Q  S  I  Q  P  F  I  S  R  C  A  V  C  E 1380      1390      1400      1410      1420      1430
         |         |         |         |         |         |
        GCTCCAGCTGTGGTGATCGCAGTTCACAGTCAGACGATCCAGATTCCCCATTGTCCTCAG
         A  P  A  V  V  I  A  V  H  S  Q  T  I  Q  I  P  H  C  P  Q 1440      1450      1460      1470      1480      1490
         |         |         |         |         |         |
        GGATGGGATTCTCTGTGGATTGGTTATTCCTTCATGATGCATACAAGTGCAGGGGCAGAA
         G  W  D  S  L  W  I  G  Y  S  F  M  M  H  T  S  A  G  A  E 1500      1510      1520      1530      1540      1550
```

FIG. 17e

```
                |              |              |              |              |              |
            GGCTCAGGTCAAGCCCTAGCCTCCCCTGGTTCCTGCTTGGAAGAGTTTCGTTCAGCTCCC
              G  S  G  Q  A  L  A  S  P  G  S  C  L  E  E  F  R  S  A  P 1560         1570         1580         1590         1600         1610
           |            |            |            |            |            |
            TTCATCGAATGTCATGGGAGGGGTACCTGTAACTACTATGCCAACTCCTACAGCTTTTGG
              F  I  E  C  H  G  R  G  T  C  N  Y  Y  A  N  S  Y  S  F  W 1620         1630         1640         1650         1660         1670
           |            |            |            |            |            |
            CTGGCAACTGTAGATGTGTCAGACATGTTCAGTAAACCTCAGTCAGAAACGCTGAAAGCA
              L  A  T  V  D  V  S  D  M  F  S  K  P  Q  S  E  T  L  K  A 1680         1690         1700         1710         1720         1730
           |            |            |            |            |            |
            GGAGACTTGAGGACACGAATTAGCCGATGTCAAGTGTGCATGAAGAGGACATAACGCGGC
              G  D  L  R  T  R  I  S  R  C  Q  V  C  M  K  R  T  -

1740         1750         1760         1770         1780         1790
           |            |            |            |            |            |
            CGCTCGAGCATGCATCTAGAGGGCCCTATTCTATAGTGTCACCTAAATGCTAGAGCTCGC
```

```
        900       910       920       930       940       950
         |         |         |         |         |         |
        CTGCCGCCTGCCTGCCTGCCACTGAGGGTTCCCAGCACCATGAGGGCCTGGATCTTCTTT
                                                  M  R  A  W  I  F  F 960       970       980       990      1000      1010
         |         |         |         |         |         |
        CTCCTTTGCCTGGCCGGGAGGGCTCTGGCAGCCCCACTAGCCGACTACAAGGACGACGAT
         L  L  C  L  A  G  R  A  L  A  A  P  L  A  D  Y  K  D  D  D 1020      1030      1040      1050      1060      1070
         |         |         |         |         |         |
        GACAAGCTAGCGAGCATGAGAGTGGGCTACACGTTGGTAAAGCACAGCCAGTCGGAACAG
         D  K  L  A  S  M  R  V  G  Y  T  L  V  K  H  S  Q  S  E  Q 1080      1090      1100      1110      1120      1130
         |         |         |         |         |         |
        GTGCCCCCGTGTCCCATCGGGATGAGCCAGCTGTGGGTGGGGTACAGCTTACTGTTTGTG
         V  P  P  C  P  I  G  M  S  Q  L  W  V  G  Y  S  L  L  F  V 1140      1150      1160      1170      1180      1190
         |         |         |         |         |         |
        GAGGGGCAAGAGAAAGCCCACAACCAGGACCTGGGCTTTGCTGGCTCCTGTCTGCCCCGC
         E  G  Q  E  K  A  H  N  Q  D  L  G  F  A  G  S  C  L  P  R 1200      1210      1220      1230      1240      1250
         |         |         |         |         |         |
        TTCAGCACCATGCCCTTCATCTACTGCAACATCAACGAGGTGTGCCACTATGCCAGGCGC
         F  S  T  M  P  F  I  Y  C  N  I  N  E  V  C  H  Y  A  R  R 1260      1270      1280      1290      1300      1310
         |         |         |         |         |         |
        AATGATAAATCTTACTGGCTCTCCACTACCGCCCCTATCCCCATGATGCCCGTCAGCCAG
         N  D  K  S  Y  W  L  S  T  T  A  P  I  P  M  M  P  V  S  Q 1320      1330      1340      1350      1360      1370
         |         |         |         |         |         |
        ACCCAGATTCCCCAGTACATCAGCCGCTGCTCTGTGTGTGAGGCACCCTCGCAAGCCATT
         T  Q  I  P  Q  Y  I  S  R  C  S  V  C  E  A  P  S  Q  A  I 1380      1390      1400      1410      1420      1430
         |         |         |         |         |         |
        GCTGTGCACAGCCAGGACATCACCATCCCGCAGTGCCCCCTGGGCTGGCGCAGCCTCTGG
         A  V  H  S  Q  D  I  T  I  P  Q  C  P  L  G  W  R  S  L  W 1440      1450      1460      1470      1480      1490
         |         |         |         |         |         |
        ATTGGGTACTCTTTCCTCATGCACACTGCCGCTGGTGCCGAGGGTGGAGGCCAGTCCCTG
         I  G  Y  S  F  L  M  H  T  A  A  G  A  E  G  G  G  Q  S  L 1500      1510      1520      1530      1540      1550
```

FIG. 17f

```
         |         |         |         |         |         |
    GTCTCACCTGGCTCCTGCCTAGAGGACTTTCGGGCCACTCCTTTCATCGAATGCAGTGGT
      V  S  P  G  S  C  L  E  D  F  R  A  T  P  F  I  E  C  S  G 1560      1570      1580      1590      1600      1610
         |         |         |         |         |         |
    GCCCGAGGCACCTGCCACTACTTTGCAAACAAGTACAGTTTCTGGTTGACCACAGTGGAG
      A  R  G  T  C  H  Y  F  A  N  K  Y  S  F  W  L  T  T  V  E 1620      1630      1640      1650      1660      1670
         |         |         |         |         |         |
    GAGAGGCAGCAGTTTGGGGAGTTGCCTGTGTCTGAAACGCTGAAAGCTGGGCAGCTCCAC
      E  R  Q  Q  F  G  E  L  P  V  S  E  T  L  K  A  G  Q  L  H 1680      1690      1700      1710      1720      1730
         |         |         |         |         |         |
    ACTCGAGTCAGTCGCTGCCAGGTGTGTATGAAAAGCCTGTAGGGTGGCACCTGCCACGGG
      T  R  V  S  R  C  Q  V  C  M  K  S  L  -

1740      1750      1760      1770      1780      1790
         |         |         |         |         |         |
    CCCTATTCTATAGTGTCACCTAAATGCTAGAGCTCGCTGATCAGCCTCGACTGTGCCTTC
```

FIG. 17f

USE OF ISOLATED DOMAINS OF TYPE IV COLLAGEN TO MODIFY CELL AND TISSUE INTERACTIONS

CROSS REFERENCE

The present application is a continuation of application Ser. No. 09/277,665 filed Mar. 26, 1999, now U.S. Pat. No. 6,440,724 which is a continuation in part of U.S. Patent Applications SN 60/106,170 filed Oct. 29, 1998; 60/079,783 filed Mar. 27, 1998; and application Ser. No. 09/183,548 filed Oct. 30, 1998 now U.S. Pat. No. 6,384,012, which is a continuation of U.S. application Ser. No.08/800,965 filed Feb. 18, 1997, now U.S. Pat. No. 5,856,184, which is a continuation of U.S. application Ser. No.08/497,206 filed Jun. 30, 1995 now U.S. Pat. No. 5,691,182, all of which are herein incorporated by reference in their entirety.

FIELD OF THE INVENTION

This invention relates to methods and kits for inhibiting angiogenesis, tumor growth and metastasis, and endothelial cell interactions with the extracellular matrix.

BACKGROUND OF THE INVENTION

Angiogenesis, the process of formation of new blood vessels, plays an important role in physiological processes such as embryonic and postnatal development as well as in wound repair. Formation of blood vessels can also be induced by pathological processes involving inflammation (e.g., diabetic retinopathy and arthritis) or neoplasia (e.g., cancer) (Folkman, 1985, Perspect, Biol. Med., 29, 10). Neovascularization is regulated by angiogenic growth factors secreted by tumor or normal cells as well as the composition of the extracellular matrix and by the activity of endothelial enzymes (Nicosia and Ottinetti, 1990, Lab. Invest., 63, 115).

During the initial stages of angiogenesis, endothelial cell sprouts appear through gaps in the basement membrane of pre-existing blood vessels (Nicosia and Ottinetti, 1990, supra; Schoefl, 1963, Virehous Arch, Pathol. Anat. 337, 97–141; Ausprunk and Folkman, 1977, Microvasc. Res. 14, 53–65; Paku and Paweletz, 1991, Lab. Invest. 63, 334–346). As new vessels form, their basement membrane undergoes complex structural and compositional changes that are believed to affect the angiogenic response (Nicosia, et. al., 1994, Exp. Biology, 164, 197–206). Early planar culture models have shown that basement membrane molecules modulate the attachment, migration and proliferation and organizational behavior of endothelial cells (Nicosia, et. al., 1994, supra). More recent studies with three-dimensional aortic culture models that more closely simulate angiogenic conditions during wound healing in vivo suggest that basement membrane is a dynamic regulator of angiogenesis whose function varies according to its molecular components (Nicosia, 1994, supra).

A common feature of all solid tumor growth is the requirement for a blood supply. Therefore, numerous laboratories have focused on developing anti-angiogenic compounds based on growth factors and their receptors. While this approach has led to some success, the number of growth factors known to play a role an angiogenesis is large. Therefore, the possibility exists that growth factor antagonists may have only limited use in treating cancer since tumors and associated inflammatory cells likely produce a wide variety of factors that can induce angiogenesis.

In this regard, a strategy that targets a common feature of angiogenesis, such as endothelial cell adhesion to the extracellular matrix (ECM), might be expected to have a profound physiological impact on tumor growth in humans. This notion is supported by the fact that antagonists of specific ECM cell adhesion receptors such as $\alpha v \beta 3$ and $\alpha v \beta 5$ integrins can block angiogenesis. Furthermore, the $\alpha v \beta 3$ integrin is expressed most prominently on cytokine—activated endothelial and smooth muscle cells and has been shown to be required for angiogenesis. (Vamer et al., Cell Adhesion and Communication 3:367–374 (1995); Brooks et al., Science 264:569–571 (1994)). Based on these findings, a potentially powerful new approach to anti-angiogenic therapy might be to specifically target critical regulatory domains within distinct ECM components.

The basement membrane (basal lamina) is a sheet-like extracellular matrix (ECM), which is a basic component of all tissues. The basal lamina provides for the compartmentalization of tissues, and acts as a filter for substances traveling between tissue compartments. Typically the basal lamina is found closely associated with an epithelium or endothelium in all tissues of an animal including blood vessels and capillaries. The basal lamina components are secreted by cells and then self assemble to form an intricate extra-cellular network. The formation of biologically active basal lamina is important to the development and differentiation of the associated cells.

Type IV collagen has been shown to be a major structural component of basement membranes. The protomeric form of type IV collagen is formed as a heterotrimer made up from a number of different subunit chains called $\alpha 1(IV)$ through $\alpha 6(IV)$. Up to now, six genetically distinct $\alpha$-chains belonging to two classes with extensive homology have been identified, and their relative abundance has been demonstrated to be tissue specific. The type IV collagen heterotrimer is characterized by three distinct structural domains: the non-collagenous (NC1) domain at the carboxyl terminus; the triple helical collagenous domain in the middle region; and the 7S collagenous domain at the amino terminus. (Martin, et. al., 1988, Adv. Protein Chem. 39:1–50; Gunwar, et. al. 1991, J. Biol. Chem. 266:14088–14094).

The capability of expression of recombinant $\alpha(IV)$ NC1 domains provides the opportunity to study the effect of specific domains on many biological processes, such as angiogenesis, tumor metastasis, cell binding to basement membranes, and assembly of Type IV collagen molecules.

SUMMARY OF THE INVENTION

The instant invention provides methods and kits for inhibiting angiogenesis, tumor growth and metastasis, and endothelial cell interaction with the extracellular matrix, each method comprising contacting the tumor or animal tissue with an one or more isolated type IV collagen NC1 $\alpha$ chain monomer selected from the group consisting of $\alpha 1$, $\alpha 2$, $\alpha 3$, and $\alpha 6$ NC1 chain monomers.

BRIEF DESCRIPTION OF THE DRAWINGS

FIGS. 17 A–F provides the sequences of each type IV collagen α chain monomer.

DESCRIPTION OF THE PREFERRED EMBODIMENTS

Figure 1:
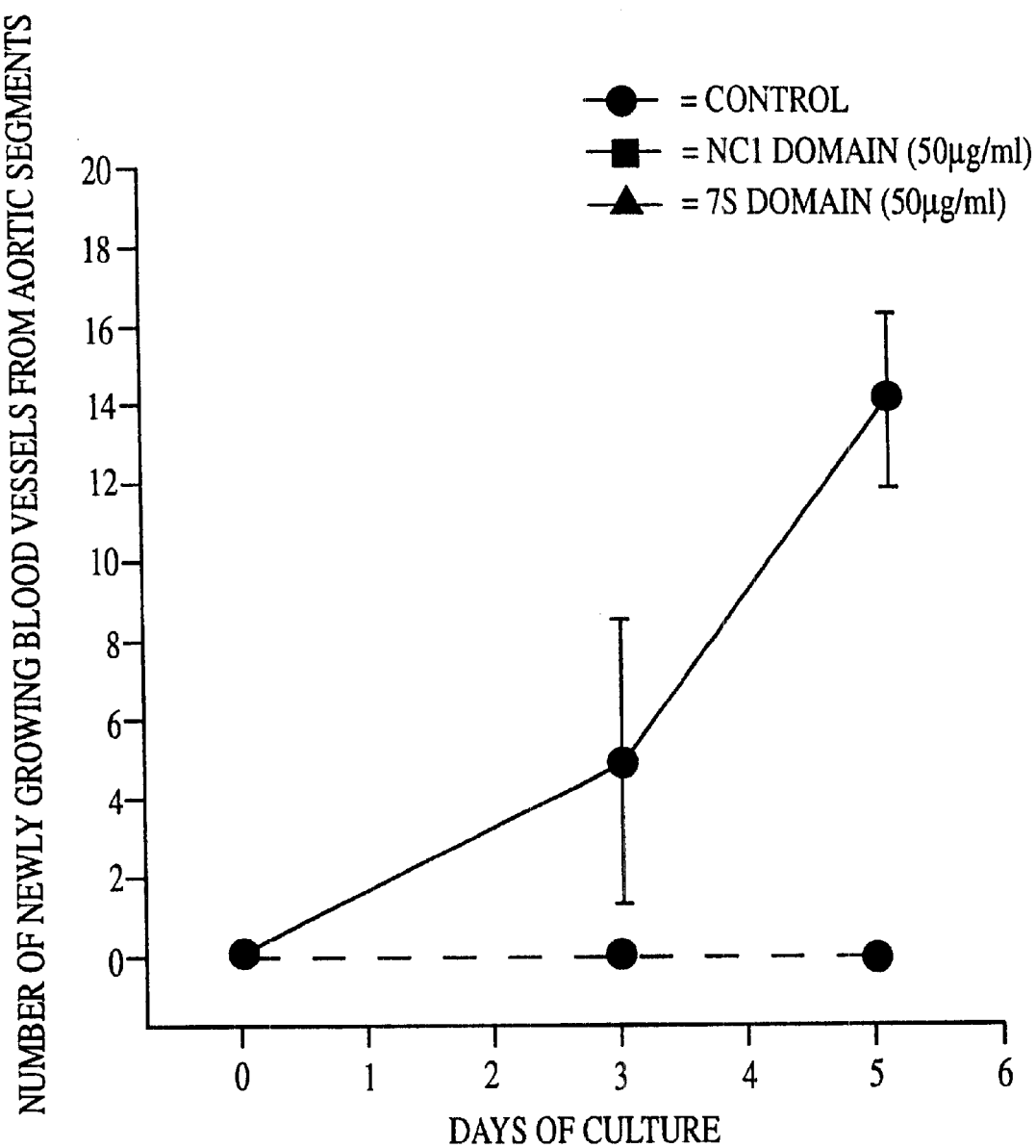
FIG. 1 illustrates the effects of NC1 (Hexamer) and 7S domains of Type IV collagen at a 50 µg/ml concentration on angiogenesis from mouse thoracic aorta organ cultures.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., 1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), and *Gene Transfer and Expression Protocols*, pp. 109–128, ed. E. J. Murray, The Humana Press Inc., Clifton, N.J.).

As used herein, the term Type IV collagen domain encompasses the group of molecules including the non-collagenous NC1 domain (Hexamer) and 7S collagenous domains, as well as NC1 α chain monomers.

The invention comprises methods for using Type IV collagen NC1 α-monomers (ie: α1, α2, α3, and α6), which are defined to include such monomers isolated from any multicellular organism or produced via recombinant protein expression from a gene encoding such a monomer from any multicellular organism, and also to encompass various modifications, additions, and/or deletions to such monomers.

In one aspect, the present invention provides methods and kits for inhibiting angiogenesis in an animal tissue comprising contacting the tumor or animal tissue with an amount effective to inhibit angiogenesis of a polypeptide composition comprising one or more isolated type IV collagen NC1 α chain monomer selected from the group consisting of α1, α2, α3, and α6 NC1 chain monomers.

In another aspect, the present invention provides methods and kits for inhibiting tumor growth in tissue comprising contacting the tumor or tissue with an amount effective to inhibit tumor growth of a polypeptide composition comprising one or more isolated type IV collagen NC1 α chain monomer selected from the group consisting of α1, α2, α3, and α6 NC1 chain monomers.

In another aspect, the present invention provides methods and kits for inhibiting tumor metastasis in tissue comprising contacting the tumor or tissue with an amount effective to inhibit metastasis of a polypeptide composition comprising one or more isolated type IV collagen NC1 α chain monomer selected from the group consisting of α1, α2, α3, and α6 NC1 chain monomers.

In a further aspect, the present invention provides methods and kits for inhibiting endothelial cell interactions with the extracellular matrix in tissue comprising contacting the tumor or tissue with an amount effective to inhibit endothelial cell interactions with the extracellular matrix of a polypeptide composition comprising one or more isolated type IV collagen NC1 α chain monomer selected from the group consisting of α1, α2, α3, and α6 NC1 chain monomers.

The NC1-encoding domain of each of the six α chain cDNAs has been cloned into a vector for recombinant protein expression as previously described (Sado et al., Kidney Intl. 53:664–671 (1998), incorporated by reference herein in its entirety). The vectors are used to stably transfect human kidney 293 cells, which produce the recombinant protein. The DNA and deduced amino acid sequences of the recombinant type IV collagen alpha chain monomers produced as described are shown in FIGS. 17A–F. The first 17 amino acids corresponds to a BM40 signal sequence (which is cleaved from the mature protein), to facilitate protein secretion. All the secreted proteins (ie: mature proteins) start with the sequence APLA followed by the affinity tag, DYKDDDDK at the amino terminus. This tag facilitates purification and identification of the material, and does not interfere with biological activity of the recombinant NC1 α chain monomer.

The type IV collagen NC1 α chain monomers can be produced by any method known in the art, including using recombinant DNA technology or biochemical peptide synthesis technology, or by isolating the NC1 domains from animal sources, such as from basement membrane sources such as bovine lens capsule and bovine kidney glomeruli. (Peczon et al., Exp. Eye Res. 30:155–165 (1980); Langeveld et al., J. Biol. Chem. 263:10481–10488 (1988); Gunwar et al., J. Biol. Chem. 266:14088–14094 (1991))

In practicing the invention, the amount or dosage range of type IV collagen NC1 α chain monomers employed is one that effectively inhibits angiogenesis, tumor growth, tumor metastasis, and/or endothelial cell-extracellular matrix interactions. An inhibiting amount of NC1 α chain monomers that can be employed ranges generally between about 0.01 μg/kg body weight and about 10 mg/kg body weight, preferably ranging between about 0.05 μg/kg and about 5 mg/kg body weight.

The NC1 α chain monomers may be administered by any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intraarterial, intramuscular, intrasternal, intratendinous, intraspinal, intracranial, intrathoracic, infusion techniques or intraperitoneally. In preferred embodiments, the NC1 α chain monomers are administered intravenously or subcutaneously.

The NC1 α chain monomers may be made up in a solid form (including granules, powders or suppositories) or in a liquid form (e.g., solutions, suspensions, or emulsions). The NC1 α chain monomers of the invention may be applied in a variety of solutions. Suitable solutions for use in accordance with the invention are sterile, dissolve sufficient amounts of the NC1 α chain monomers, and are not harmful for the proposed application.

The NC1 α chain monomers may be subjected to conventional pharmaceutical operations such as sterilization and/or may contain conventional adjuvants, such as preservatives, stabilizers, wetting agents, emulsifiers, buffers etc.

For administration, the NC1 α chain monomers are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The present invention may be better understood with reference to the accompanying examples that are intended for purposes of illustration only and should not be construed to limit the scope of the invention, as defined by the claims appended hereto.

EXAMPLE 1

In Vitro Effect on Angiogenesis

With modifications, the procedures of Nicosia and Ottinetti (1990), supra, and Nicosia, et. al. (1994), supra, were utilized for experiments designed to test the effect of Type IV collagen on angiogenesis under in vitro conditions. The model has been used to study the effects of growth factors and extracellular matrix molecules on the angiogenic response and employs aortic rings cultures in three-dimensional collagen gels under serum-free conditions. These experiments are outlined below.

A. Methods

Experiments were performed with 1–3 month old Swiss Webster male mice. Following anesthesia, the thoracic aorta was excised under aseptic conditions and transferred to sterile MCDB 131 sterile growth medium (Clonetics, San Diego, Calif.) containing antibiotics. Fat was dissected away from the aorta and approximately six to eight 1 mm thoracic segments were obtained from each specimen. Segments were transferred to 48 well tissue culture plates. The wells of these plates were layered with 100 microliters of Matrigel (EHS basement membrane, Collaborative Biomedical Products, Bedford, Mass.) prior to transfer of the aortic segments. The Matrigel was diluted 1:1 with MCDB 131 growth medium prior to use. The segments were centered in the wells and an additional 100 microliters of Matrigel was then placed over the specimens. The aortic segments were therefore embedded in the basement membrane matrix. Each well then received 300 microliters of MCDB 131 growth medium. The plates were placed in an incubator maintained at 37° C. with 5% $CO_2$. Specimens were observed daily over a 7 day period. Newly growing microvessels were counted using an inverted phase microscope at various times during the culture period, but data is expressed at 3 and 5 days of culture. To test for the effect of Type IV collagen on angiogenesis, domains at known concentrations were mixed with the Matrigel and with the MCDB 131 growth medium. Fresh MCDB 131 growth medium (plus and minus collagen domains) was changed every 3 days.

B. Results

Figure 2:
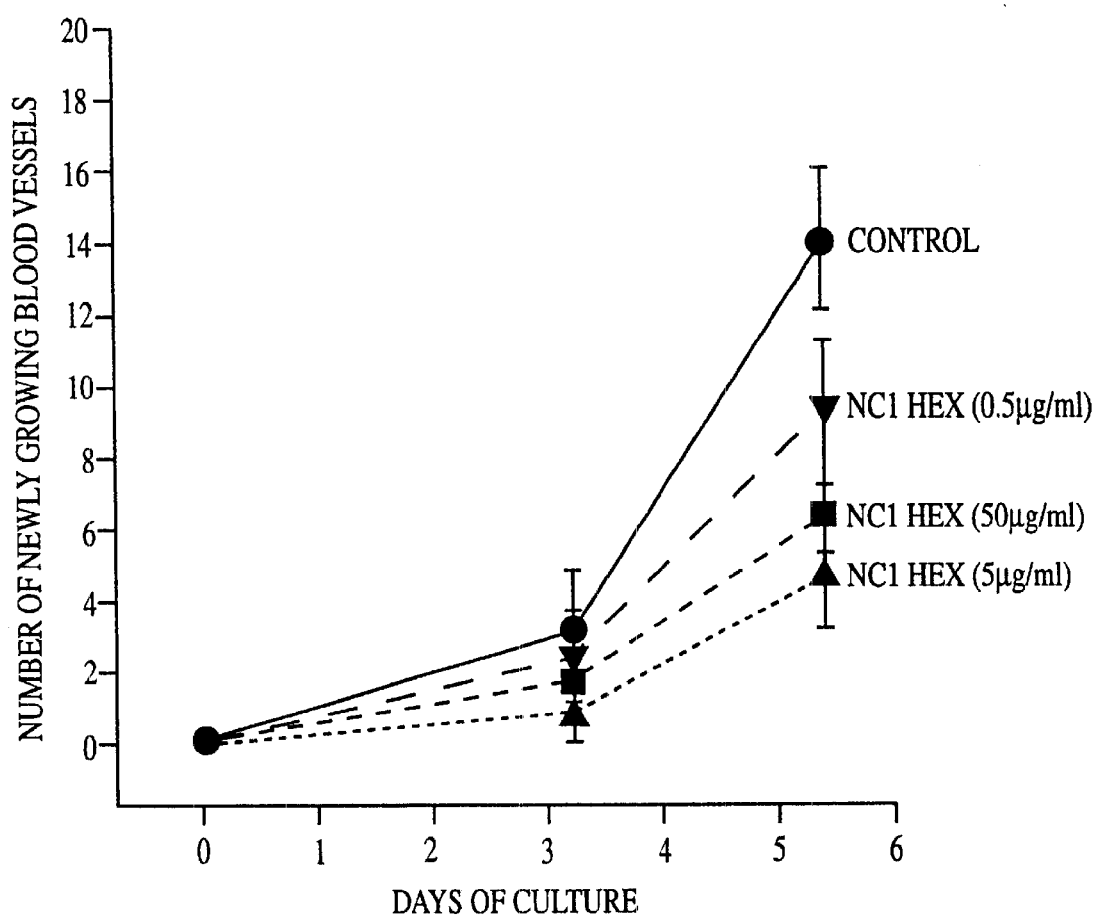
FIG. 2 illustrates the effects of 7S domain of Type IV collagen on angiogenesis from mouse thoracic aorta organ cultures. The domain concentrations employed in this experiment were 0 µg/ml (control); 0.5 µg/ml; 5 µg/ml and 50 µg/ml.
Figure 3:
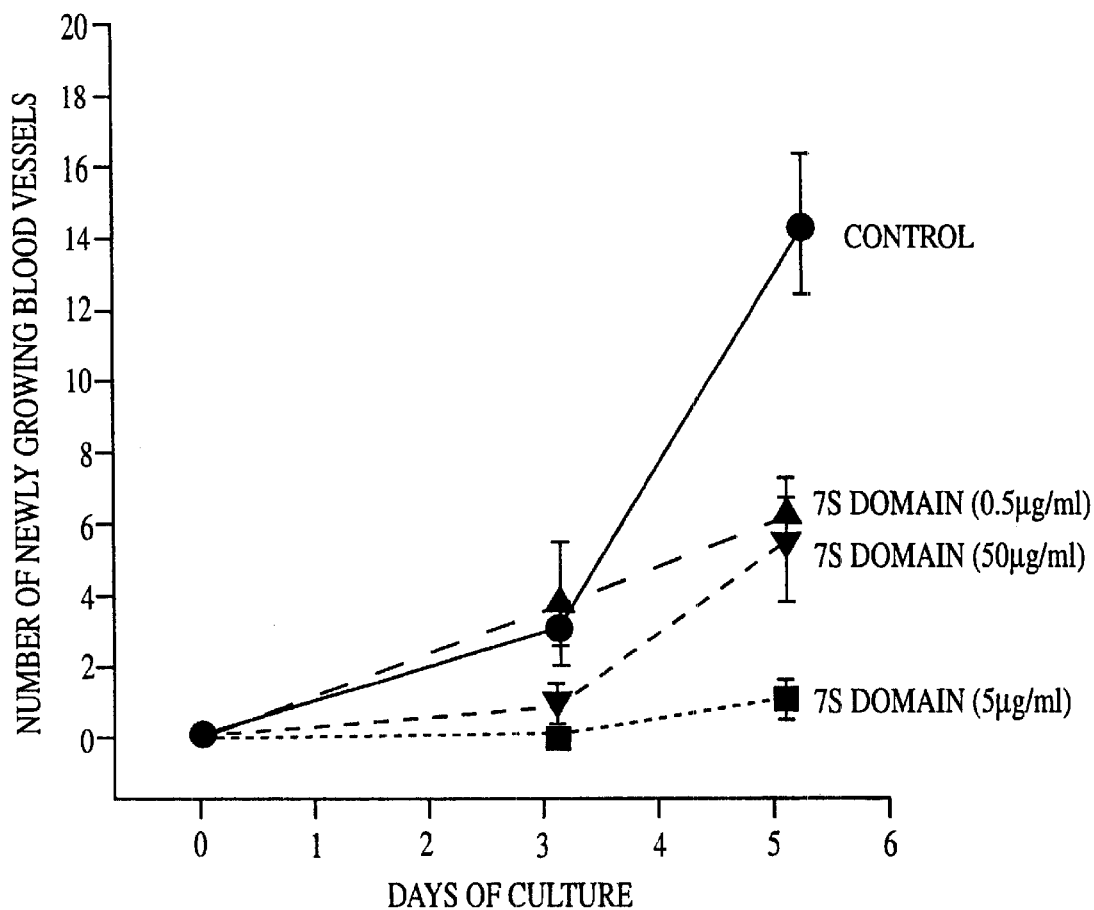
FIG. 3 illustrates the effects of NC1 (Hexamer) domain of Type IV collagen on angiogenesis from mouse thoracic aorta organ cultures. The domain concentrations employed in this experiment were 0 µg/ml (control); 5 µg/ml and 5 µg/ml and 50 µg/ml.

After establishing the time course of angiogenesis under control conditions (Matrigel plus MCDB 131 growth medium), experiments were performed using various concentrations of Type IV collagen (isolated from bovine lens) NC1 (hexamer) and 7S domains. Data represents the analysis of at least 3 specimens per experimental condition. In the first experiment (FIG. 1), analysis indicated that at a concentration of 50 μg/ml, NC1 domain and 7S domain significantly inhibited angiogenesis as monitored at 3 and 5 days of culture. In the second experiment, various concentrations of these domains were analyzed. As indicated in FIG. 3, 7S domain at 50 μg/ml again significantly inhibited angiogenesis at 3 and 5 days. Inhibition was reduced at 5 and 0.5 μg/ml concentrations. As indicated in FIG. 2, NC1 domain was less effective in blocking angiogenesis as compared to that observed in the first experiment (FIG. 1), although it was still effective. In addition, as compared to the 7S domain, there was less of a correlation between concentration and inhibitory action.

Figure 4A:
FIG. 4 are photographs of mouse thoracic aorta segments embedded in Matrigel (EHS basement membrane matrix, Collaborative Biomedical Products, Bedford, Mass.) at 5 days of culture. Control specimen (0 µg/ml of NC1 (Hexamer) and 7S domains) exhibited growth of microvessels from the cultured tissue into the matrix (FIG. 4A). In contrast, angiogenesis was inhibited in specimens cultured with 50 µg/ml of 7S domain (FIG. 4B) and NC1 (Hexamer) domain (FIG. 4C).
Figure 4B:
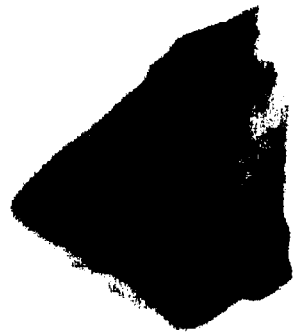
Figure 4C:

FIGS. 4A–C are photographs of mouse thoracic aorta segments embedded in Matrigel (EHS basement membrane matrix, Collaborative Biomedical Products, Bedford, Mass.) at 5 days of culture in the presence or absence of 50 μg/ml of Type IV collagen domains. The control specimen (no domains) exhibited growth of microvessels from the cultured tissue into the matrix (FIG. 4A). In contrast, angiogenesis inhibition was observed in tissues cultured in the presence of 50 μg/ml of 7S (FIG. 4B) and NC1 (Hexamer) domain (FIG. 4C).

EXAMPLE 2

Subcutaneous Fibrin Implant Angiogenesis

Recombinant human type IV collagen NC1 (α3) monomer (Sado et al., Kidney International 53:664–671 (1998))

was injected intravenously in Fisher 344 rats containing fibrin implants surgically placed subcutaneously, a modified version of the method described by Dvorak et al (Lab. Invest. 57(6):673–686 (1987)). The implants were then removed and directly analyzed using an inverted microscope. The analysis involved counting the number of blood vessels that had grown into the fibrin in the control and experimental group.

Briefly, 4 fibrin implants were surgically implanted subcutaneously into Fisher 344 rats (2 dorsal and 2 ventral sides). The average rat weight was approximately 125 grams.

Three rats (EXP) were given tail vein injections of either control (fibrin alone), 100 μl of 100 μg/ml of 7S domain of type IV collagen (approximately 0.80 mg/kg body weight), 100 μl of 100 μg/ml of type IV collagen hexamer (approximately 0.80 mg/kg body weight), or recombinant collagen type IV NC1 (α3) monomer at a concentration of 1.26 mg/ml in PBS (120 μg protein, or approximately 0.96 mg/kg body weight) and 3 rats (C) were given 100 μl tail vein injections of PBS. Injections of recombinant protein were given every other day for five doses. The injection schedule was as follows:

Day 1: (implant day) injection and remove blood sample (EXP and C)
Day 3: Injection (EXP and C)
Day 5: Injection and remove blood sample (EXP and C)
Day 7: Injection (EXP and C)
Day 9: Injection and remove blood sample (EXP and C)
Day 11: Remove and fix implants (save blood sample) (EXP and C)

The results of one experiment were as follows:

| 2 week in vivo experiment: | |
|---|---|
| Control (fibrin alone) | about 66 BV |
| 7S domain of type IV lens collagen (100 μg/ml) | None |
| Hexamer of type IV lens collagen (100 μg/ml) | None |
| Monomer (α3) | None |

The results are shown as the mean number of blood vessels per implant. The results of this study demonstrate that isolated domains of type IV collagen, including the α3 monomer, can significantly inhibit capillary growth in the in vivo fibrin clot implant model. In subsequent experiments, the inhibitory effect was occasionally seen to attenuate with time, suggesting that higher dosages or more frequent injections might be even more effective.

Figure 5:
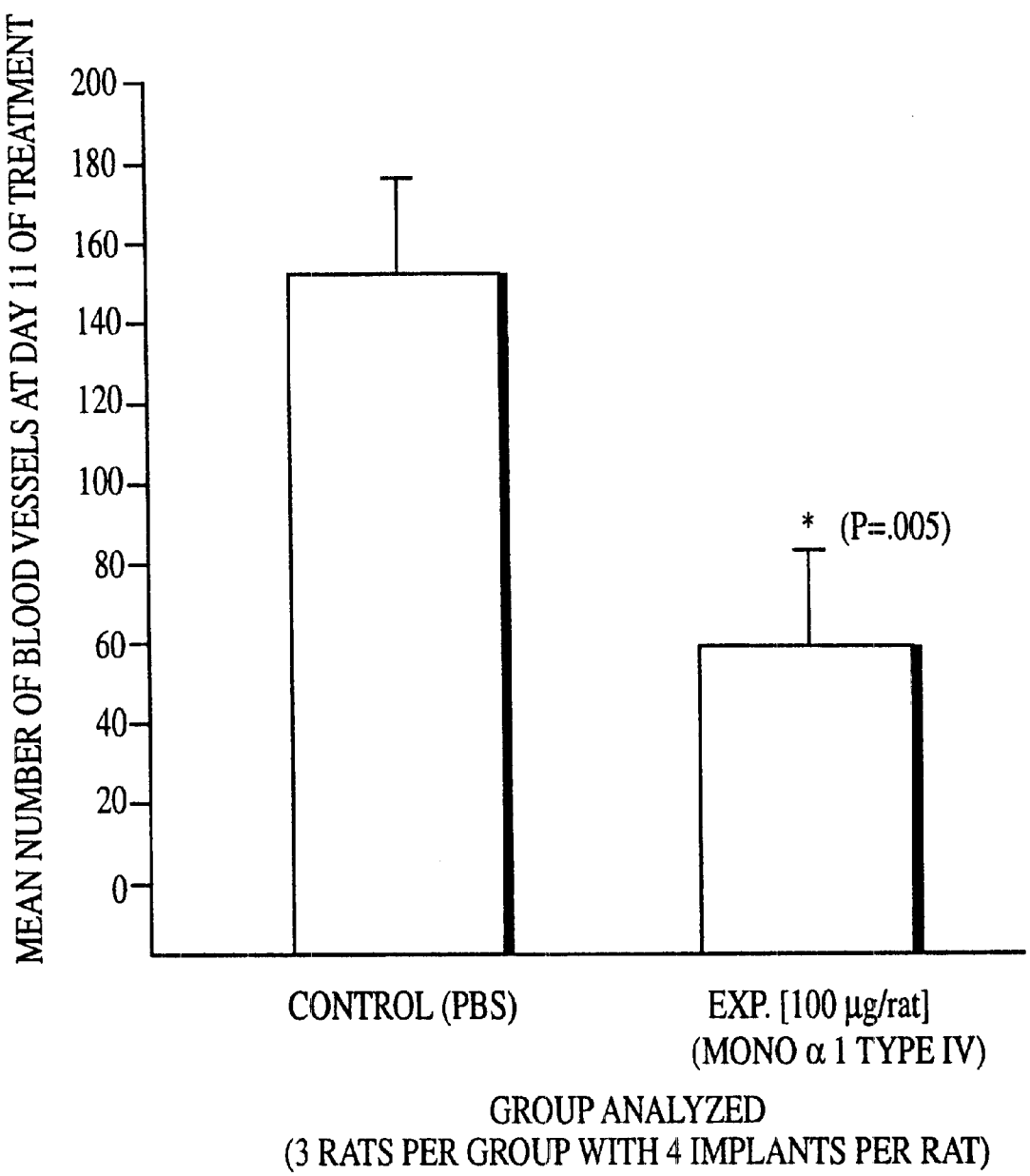
FIG. 5 is a graphical representation of data demonstrating the in vivo effect of IV injection of recombinant (α1) type IV collagen monomer on angiogenesis using fibrin implants in rats.
Figure 6:
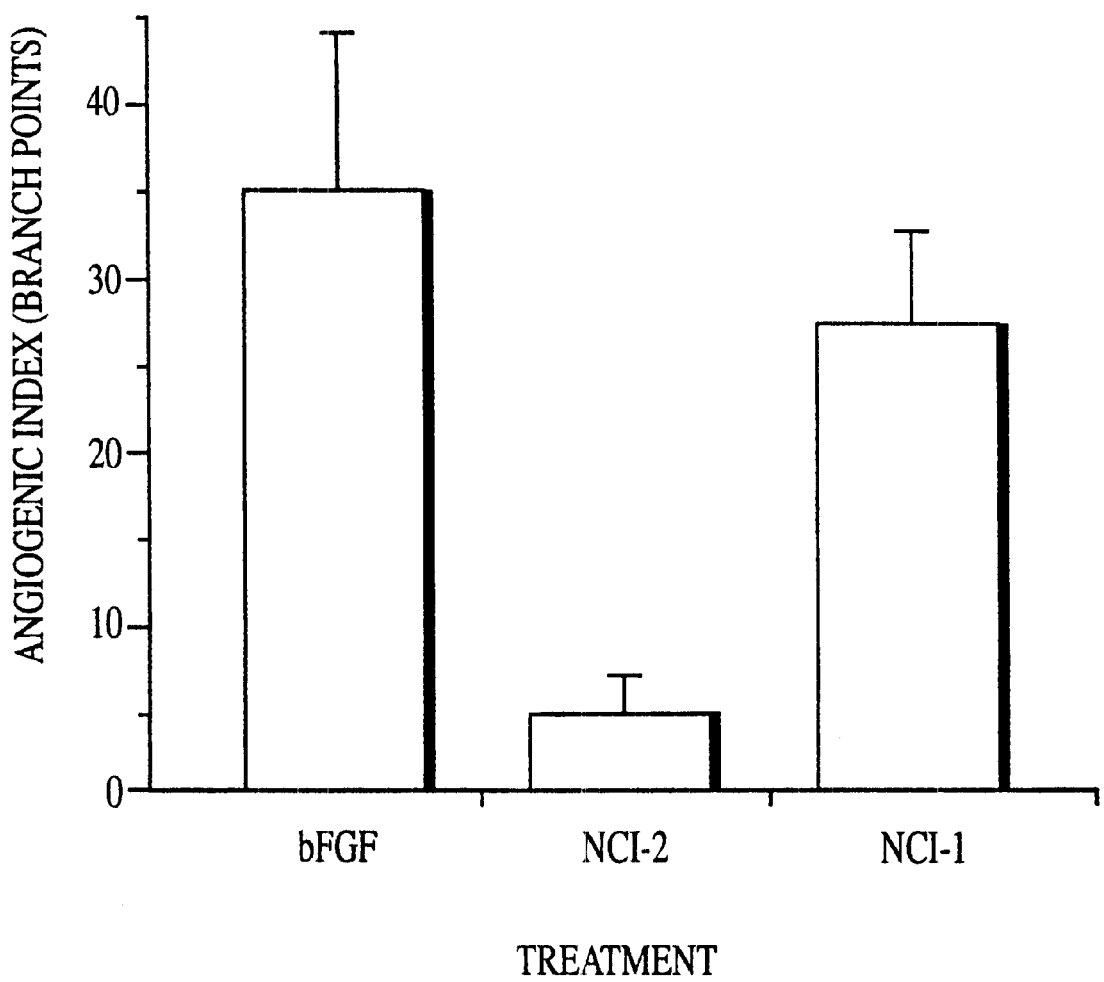
FIG. 6 is a graphical representation of data demonstrating that the recombinant (α1) and (α2) NC1 monomers inhibit the bFGF-induced increase in angiogenic index in vivo.
Figure 7:
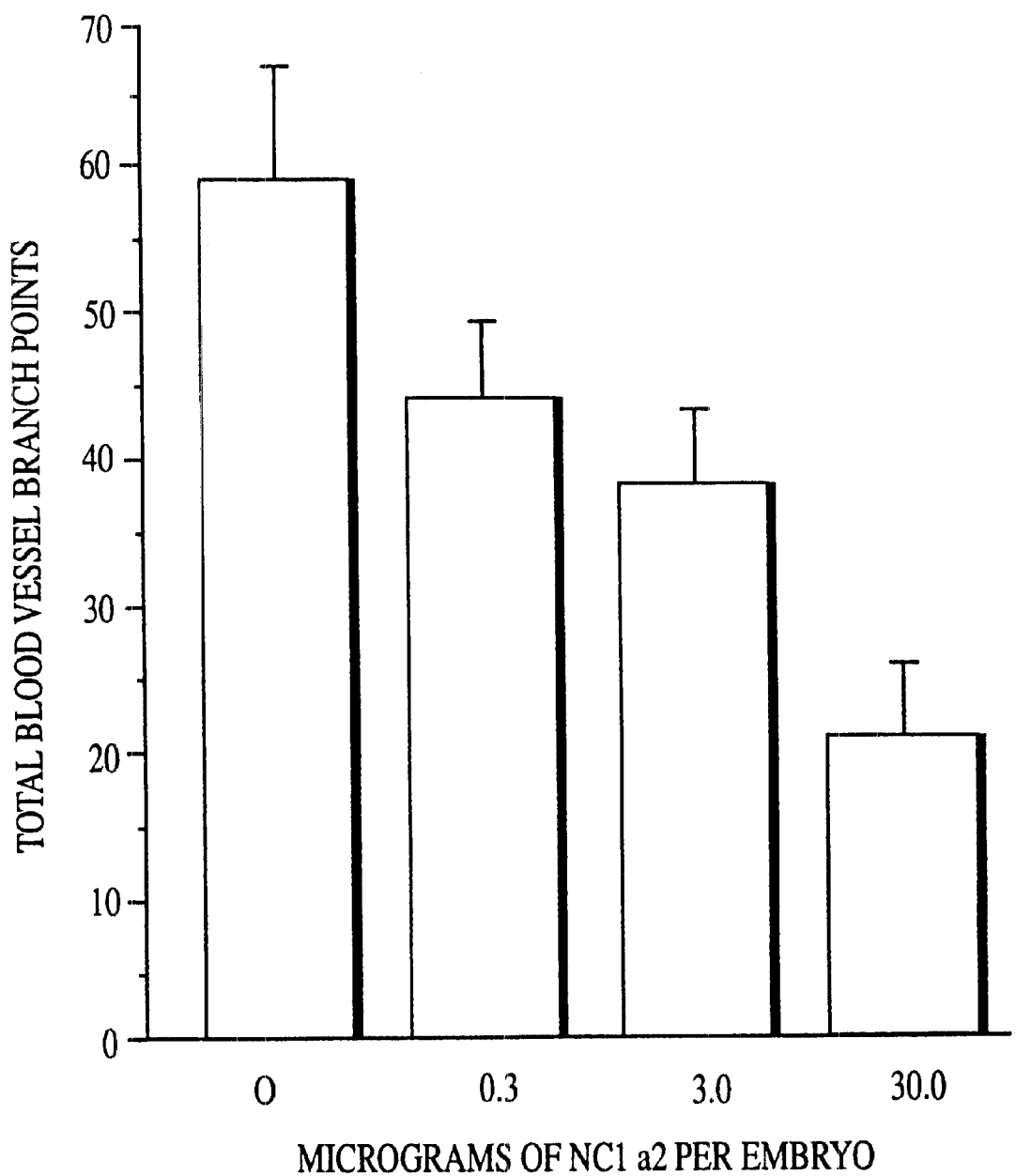
FIG. 7 is a graphical representation of demonstrating the dose response effect of recombinant (α2) NC1 monomer on the bFGF-induced increase in total blood vessel branch points in vivo.
Figure 8:
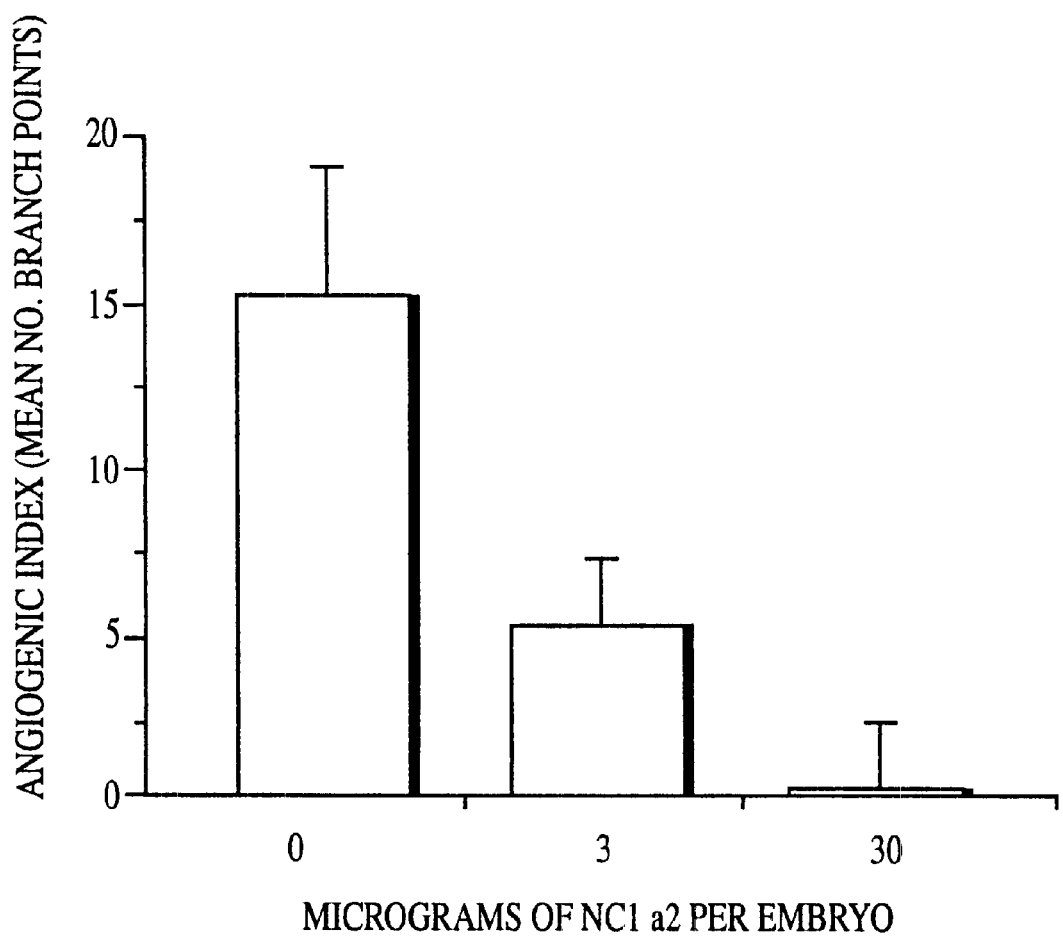
FIG. 8 is a graphical representation of data demonstrating the dose response effect of recombinant (α2) NC1 monomer on the bFGF-induced increase in angiogenic index in vivo.
Figure 9:
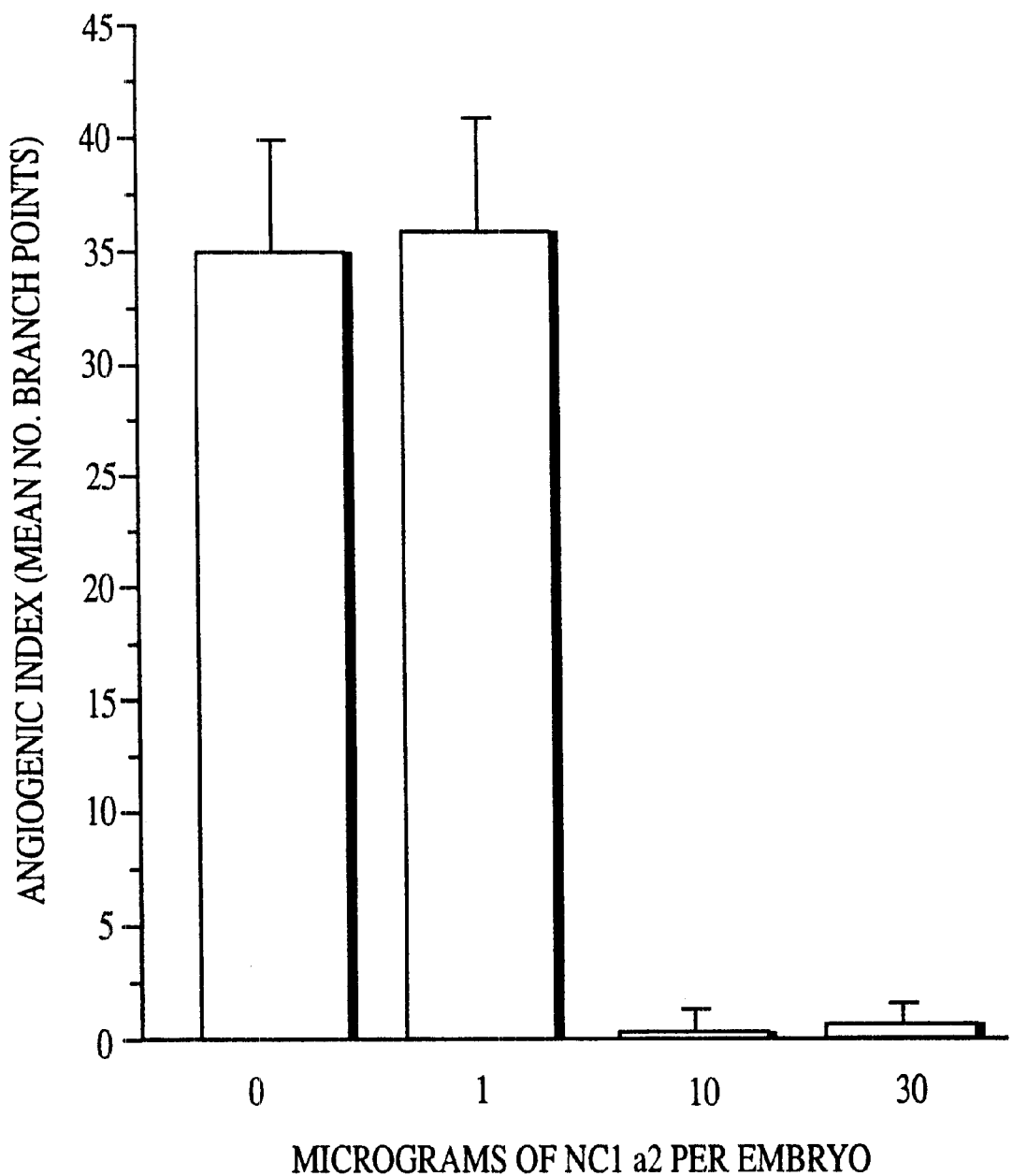
FIG. 9 is a graphical representation of data demonstrating the dose response effect of recombinant (α2) NC1 monomer on the bFGF-induced increase in angiogenic index in vivo.

A similar experiment was conducted using recombinant human type IV collagen NC1 (α1) monomer (100 μl of a 1 μg/μl solution; approximately 0.80 mg/kg body weight) and comparing the number of blood vessels that had grown into the fibrin at day 11 of treatment relative to the control group. Three rats per group were analyzed with each rat having 4 implants. These experiments demonstrated that administration of the al monomer significantly inhibited capillary growth in the in vivo fibrin clot implant model (FIG. 5).

EXAMPLE 3

Recombinant NC1 (α2) Domain Inhibits Angiogenesis in vivo

We next tested the effects of systemic administration of soluble NC1 α-chain monomers in the chick embryo CAM angiogenesis assay.

Angiogenesis was induced in the CAMs of 10 day old chick embryos with bFGF as described (Brooks et al., Cell 92:391–400 (1998)). Twenty four hours later the embryos were systemically treated with various concentrations of recombinant NC1 α-chain monomers, in a total volume of 100 μl of sterile phosphate buffered saline (PBS). Two days later the embryos were sacrificed and the filter discs and CAM tissues removed. Angiogenesis was quantitated by counting the number of angiogenic blood vessel branch points in the confined area of the filter disc. The Angiogenic Index is defined as the number of branch points from experimental treatment minus control treatment.

In initial experiments, recombinant α1 or α2 NC1 domains were injected at a concentration of 50 μg per embryo. At this concentration, the NC1 domains were shown to be highly toxic as demonstrated by greater than 90% embryo cell death. However, at lower doses they were well tolerated and showed potent anti-angiogenic activity. A total of 6 individual angiogenesis experiments were conducted with the NC1 domains. However, in two experiments, the bFGF induction was low, making it difficult to interpret the results. The NC1 α2 domain appeared to be more consistent and potent than the α1 NC1 domain at inhibiting angiogenesis. In fact, systemic administration of 30 μg of NC1 α2 consistently inhibited angiogenesis by greater than 90% (FIGS. 6–9), as measured by inhibition of the bFGF-induced increase in the angiogenic index and the mean number of blood vessel branch points. In contrast, NC1 α1 domain showed variable inhibitory activity (0%–50%) throughout the experiments.

EXAMPLE 4

Recombinant NC1 Domain Inhibits Melanoma Tumor Growth in vivo

Since the growth of all solid tumors depends on angiogenesis to provide nutrients for its continued expansion, reagents that have the capacity to inhibit angiogenesis may significantly inhibit tumor growth. Therefore, we tested the effects of recombinant NC1 domains of type IV collagen for their effects on tumor growth in vivo.

Figure 10:
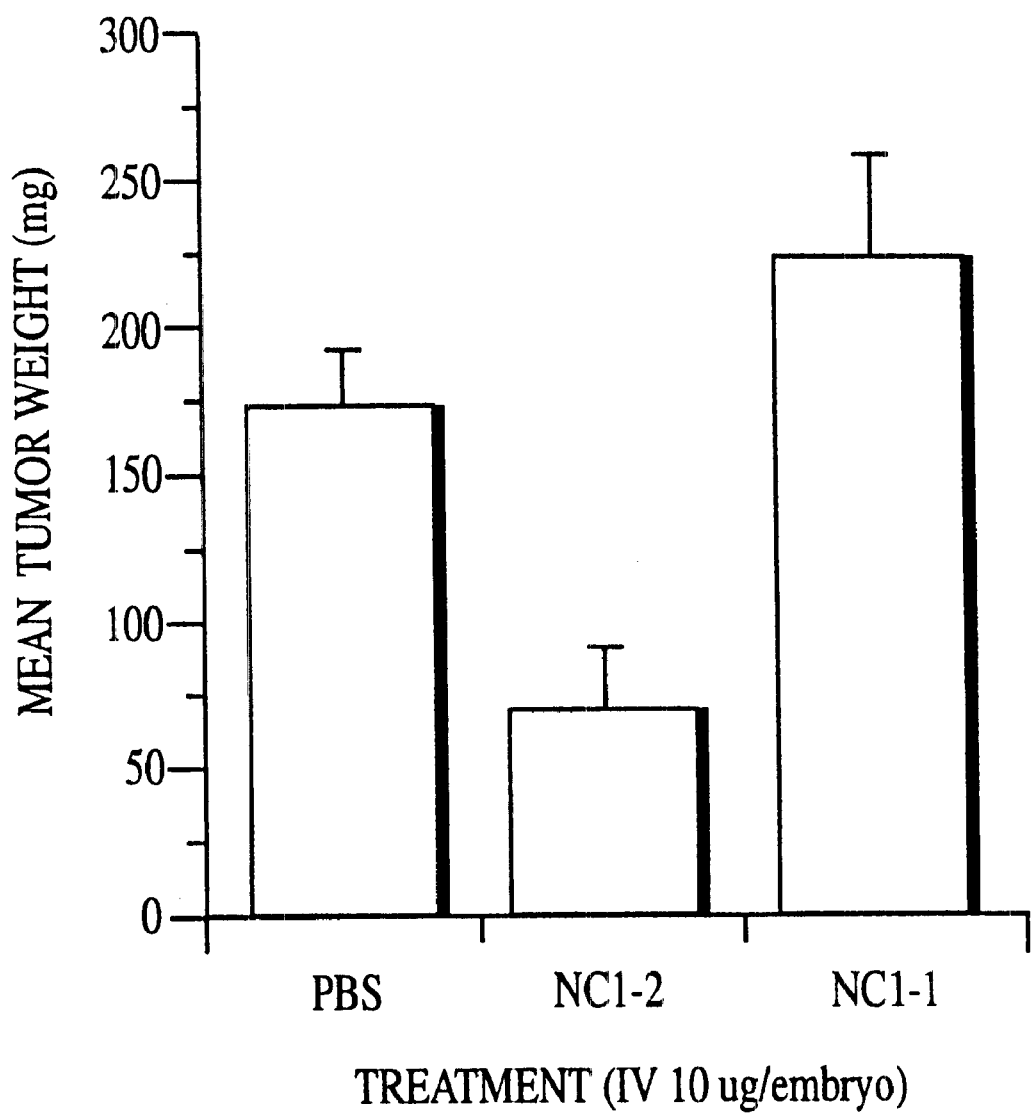
FIG. 10 is a graphical representation of data demonstrating the effect of recombinant (α1) and (α2) NC1 monomers on mean CS-1 melanoma tumor weight in vivo.
Figure 11:
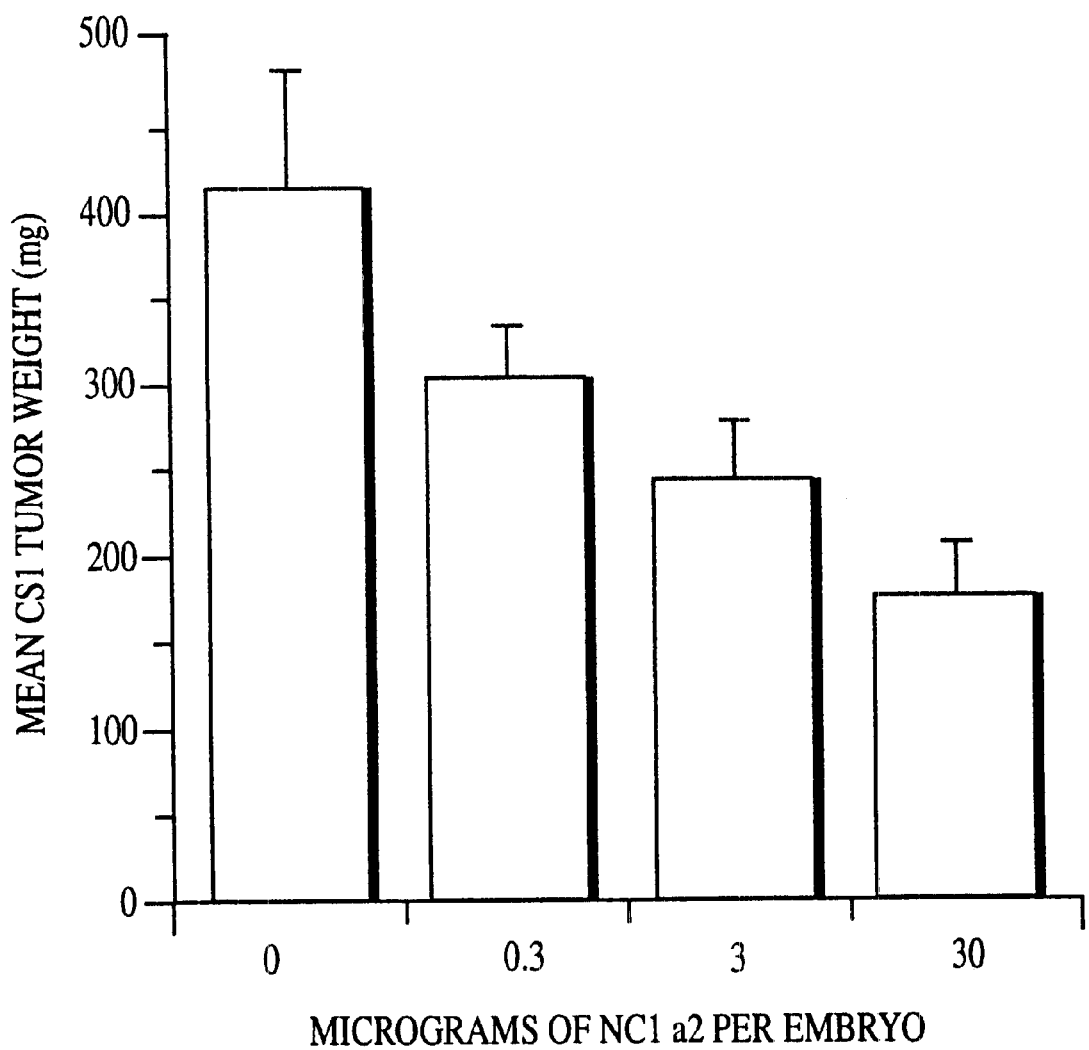
FIG. 11 is a graphical representation of data demonstrating the dose response effect of recombinant (α2) NC1 monomer on mean CS-1 melanoma tumor w eight in vivo.
Figure 12:
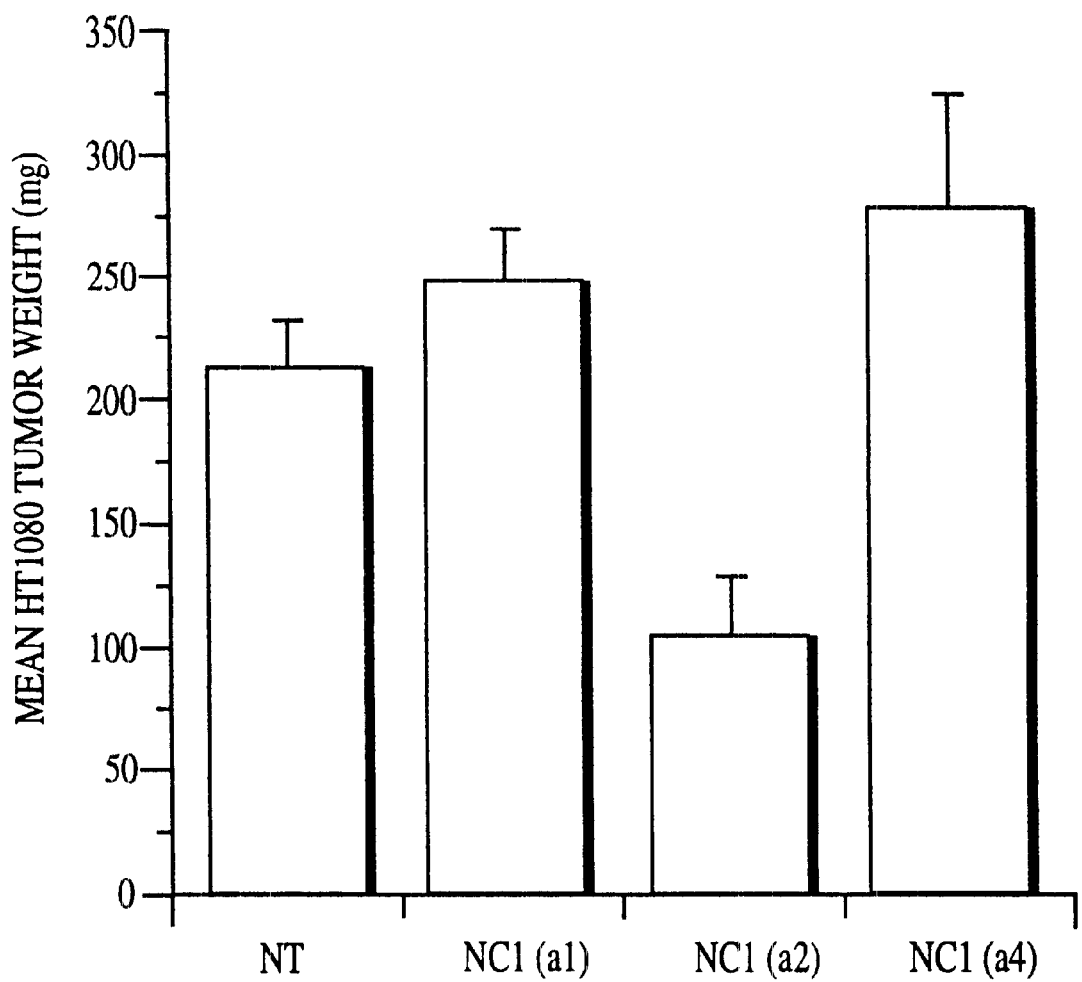
FIG. 12 is a graphical representation of data demonstrating the effect of recombinant (α1), (α2), and (α4) NC1 monomers on mean HT1080 tumor weight in vivo.
Figure 13:
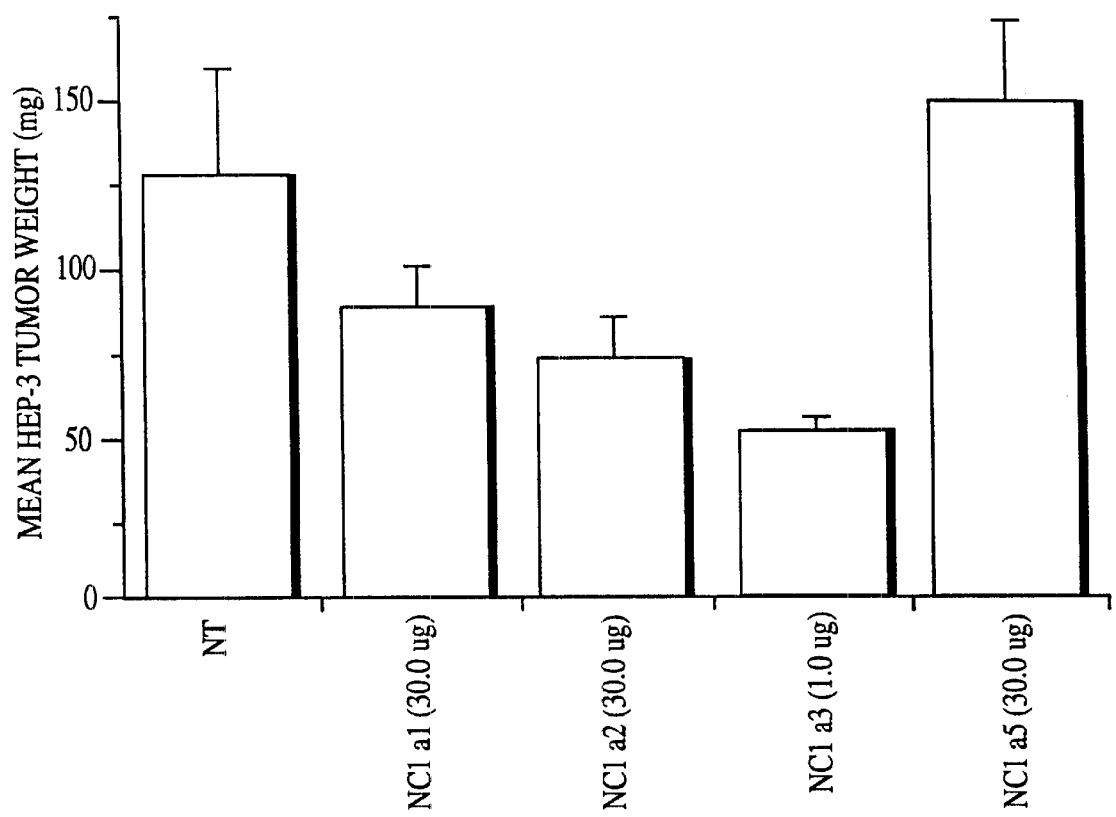
FIG. 13 is a graphical representation of data demonstrating the effect of recombinant (α1), (α2), (α3) and (α5) NC1 monomers on mean HEP-3 tumor weight in vivo.

To test the effects of NC1 domains on tumor growth in vivo, we utilized the chick embryo tumor growth assay. Briefly, single cell suspensions of 3 distinct tumor types were applied to the CAM of 10 day old chick embryos. The tumors included CS-1 Melanoma cells ($5 \times 10^6$), HT1080 human fibrosarcoma cells ($4 \times 10^5$) and Hep-3 human epidermoid carcinoma cells ($2 \times 10^5$). The embryos were injected systemically with varying concentrations of NC1 α-chain monomers 24 hours later. The embryos were next allowed to incubate for a total of 7 days, at which time they were sacrificed. The resulting tumors were resected and wet weights determined. A total of 6 tumor growth assays were conducted with the 3 distinct tumor types. A single injection of 10 μg NC1 α2 domain inhibited CS1 melanoma tumor growth by approximately 70% relative to control (FIG. 10). In similar experiments, dose response curves were completed with CS-1 tumors. Systemic administration of NC1 α2 resulted in a dose-dependent inhibition of CS-1 melanoma tumor growth in vivo with a maximum inhibition following a single dose at 30 μg (FIG. 11). Systemic administration of NC1 α1 also inhibited CS-1 tumor growth but it was variable and in some experiments failed to inhibit tumor growth (See FIG. 10). In similar experiments, NC1 α2 inhibited HT1080 human fibrosarcoma tumor growth by approximately 50% after a single systemic injection of 30 μg, while NC1 α1 and α4 had no effect (FIG. 12). Finally, systemic administration of NC1 α2 (30.0 μg) and α3 inhibited Hep-3 human epidermoid carcinoma tumor growth by approximately 40% and 60% respectively, and α1 inhibited Hep-3 tumor growth by approximately 30%, while NC1 α5 domain failed to inhibit tumor growth (FIG. 13).

We conclude from these in vivo studies that tumor growth can be inhibited by isolated NC1 α-chain monomers. These molecules can thus be used alone, or to complement the use of existing anti-tumor agents, in providing enhanced and more effective anti-tumor therapy.

EXAMPLE 5

Immobilized NC1 Domains Support Human Endothelial Cell Adhesion

In order for new blood vessels to form, endothelial cells must have the capacity to adhere and migrate through the ECM. Moreover, this endothelial cell-ECM interaction may facilitate signal transduction events required for new blood vessel formation. Therefore, since type IV-collagen is an ECM protein which is known to support cell adhesion, we tested the ability of the NC1 domains to support endothelial cell attachment.

Microtiter plates were coated with 25 μg/ml of purified NC1 domains followed by incubation with 1% bovine serum albumin (BSA) to block non-specific interactions. Human endothelial cells (ECV304) were then allowed to attach to the immobilized NC1 domains for 1 hour. Non-adherent cells were removed by washing and attached cells were quantified by measuring the optical density (O.D.) of crystal violet eluted from attached cells. Data bars represent the mean +/− standard error of the O.D. from triplicate wells.

Figure 14:
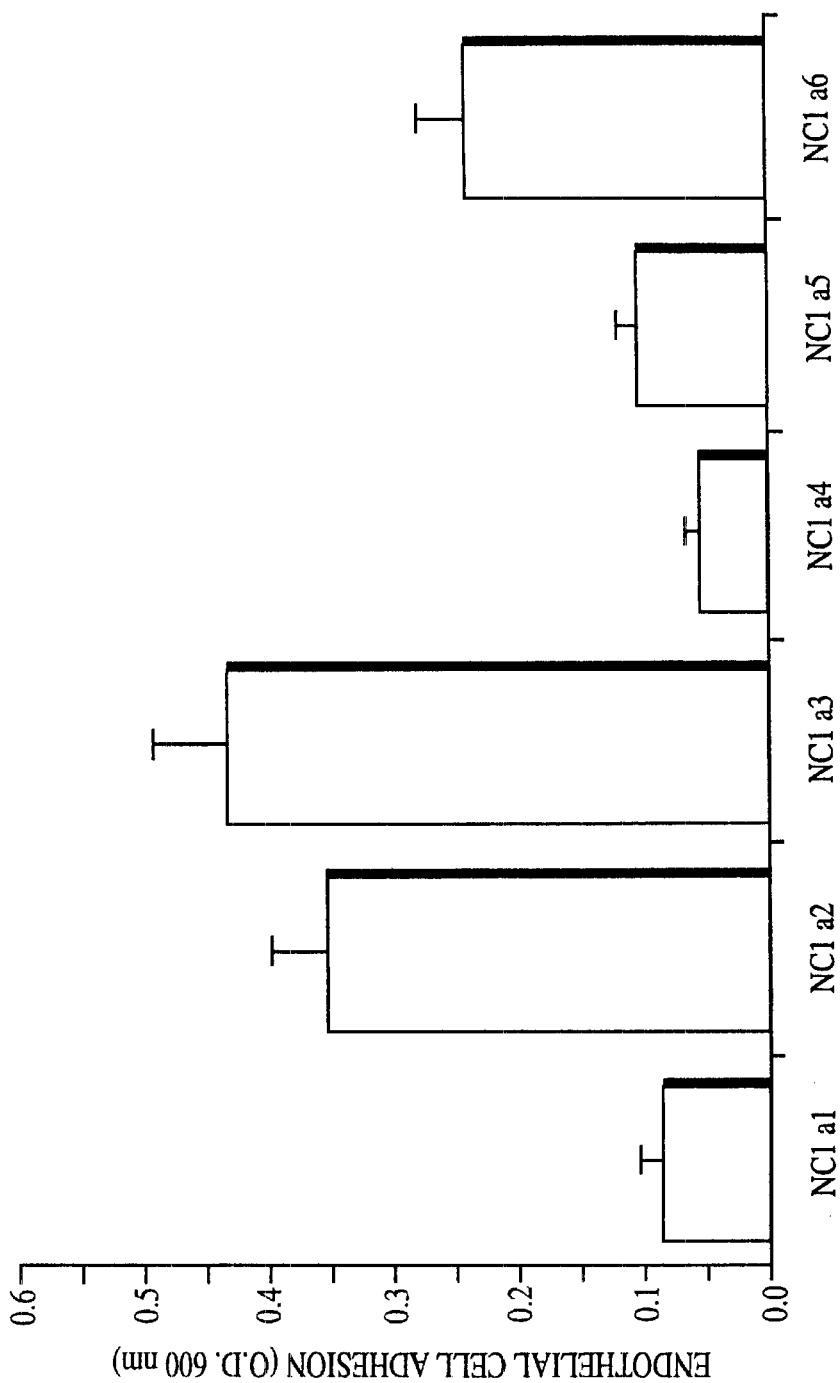
FIG. 14 is a graphical representation of data demonstrating human endothelial cell adhesion to immobilized NC1 α monomers.
Figure 15:
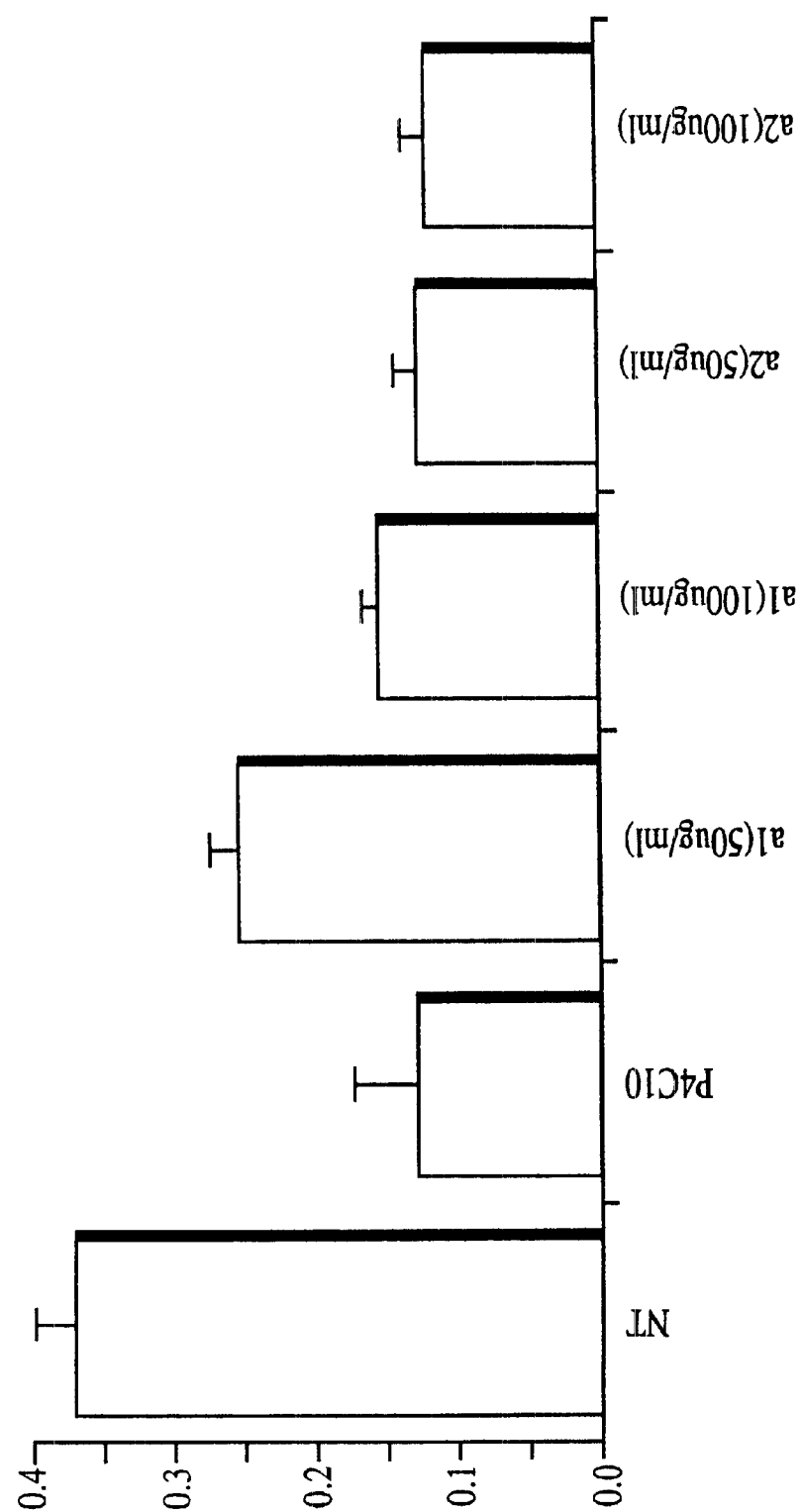
FIG. 15 is a graphical representation of data demonstrating the effect of soluble α1 and α2 NC1 monomers on human endothelial cell adhesion to pepsinized collagen type IV.

Immobilized NC1 α2, α3, and α6 domains supported endothelial cell adhesion while NC1 α1, α4, and α5 domains promoted little if any cell adhesion (FIG. 14). Soluble NC1 α1 (a1) and α2 (a2) inhibited endothelial cell adhesion to pepsinized collagen type IV by approximately 50% (FIG. 15).

Taken together, these findings demonstrate that isolated, recombinant NC1 domains from the α1, α2, α3, and α6 chains of collagen type IV can mediate human endothelial cell adhesion and/or inhibit endothelial cell adhesion to ECM proteins in vitro, and suggest that the potent anti-angiogenic and anti-tumor activity of the isolated NC1 domains is due to disruption of endothelial cell interaction with the extracellular matrix that are necessary for angiogenesis.

EXAMPLE 6

Endothelial Cell Migration

Invasive cellular processes such as angiogenesis and tumor metastasis also require cellular motility. Thus we evaluated the ability of isolated NC1 domains to support human endothelial cell migration in vitro. These experiments were conducted essentially according to the methods in Brooks et al., J. Clin. Invest. 99:1390–1398 (1997).

Figure 16:
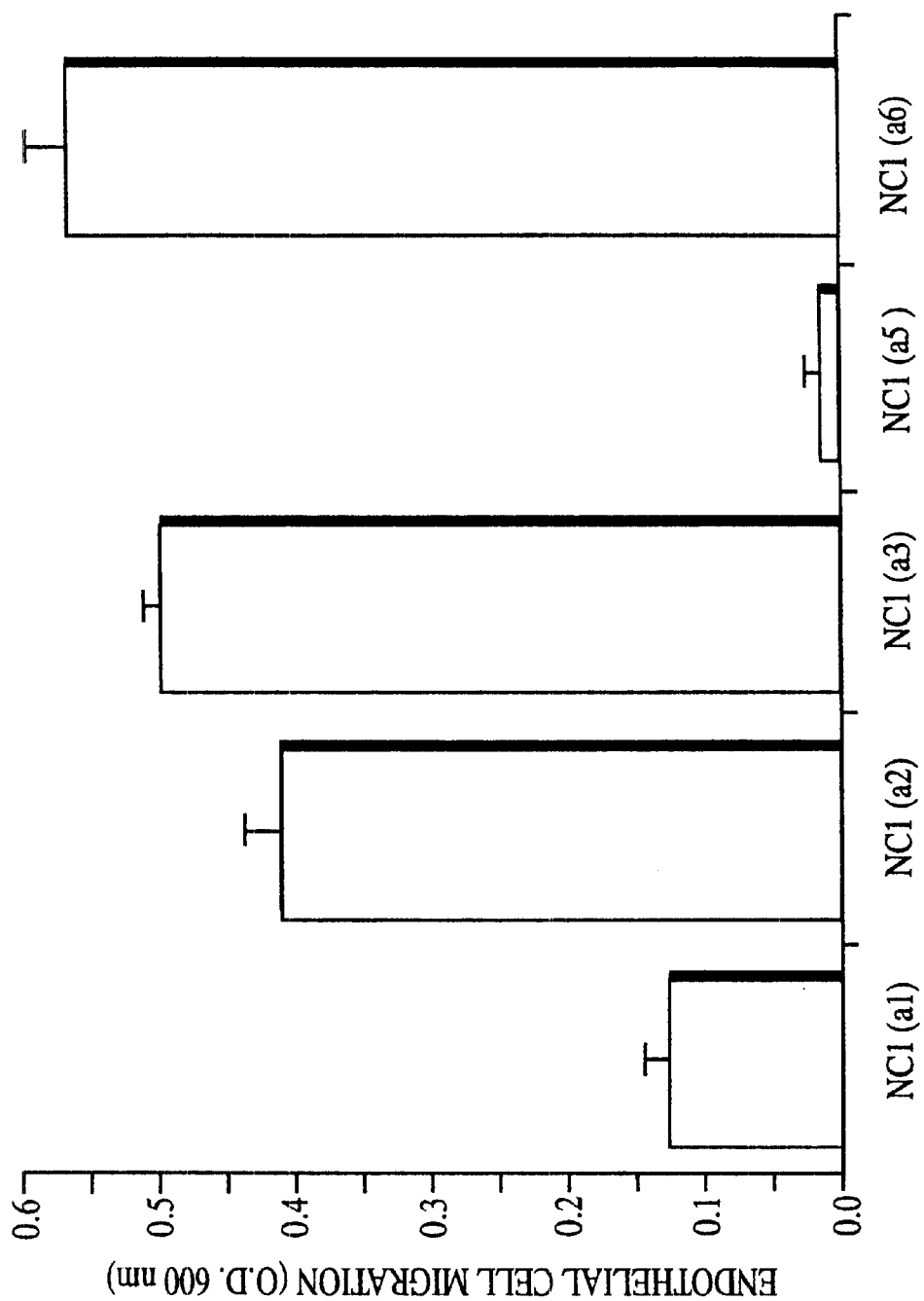
FIG. 16 is a graphical representation of data demonstrating the effect of isolated recombinant NC1 monomers on human endothelial cell migration in vitro.

The results of these experiments indicate that NC1 α2, α3, and α6 domains can support human endothelial cell migration in vitro, while α1, α4, and α5 domains showed little if any capacity to support endothelial cell migration (FIG. 16).

EXAMPLE 7

Efficacy in Lewis Lung in vivo Tumor

The above studies indicated that specific domains of collagen type IV can promote cell migration in vitro. Thus, we evaluated the ability of NC1 domains to support endothelial cell migration in vivo.

The α (IV) NC1 domain hexamer, isolated by enzymatic digestion of bovine lens capsule basement membrane by known protocols (Peczon et al., Exp. Eye Res. 30:155–165 (1980)) was tested in the metastatic Lewis lung mouse tumor model using a standard protocol which is considered to be a good model of both metastasis and angiogenesis of lung tumors. (See for example, Teicher et al., Anticancer Res. 18:2567–2573 (1998); Guibaud et al., Anticancer Drugs 8:276–282 (1997); Anderson et al., Cancer Res. 56:715–718 (1996)).

Each study consisted of an untreated control group and six treatment groups. There were ten animals per treatment group with 40 mice in the control. In each study, all treatment was administered intravenously once every 2 days for 7 doses starting one day after tumor inoculation. Dosages of α (IV) NC1 hexamer were either 100 μg/mouse or 200 μg/mouse. In the Lewis lung study, the tumor cell inoculum was $1 \times 10^6$ viable cells. All animals were weighed twice a week throughout the study. Starting one day after the last treatment, 5 mice were periodically sacrificed from each control group to measure pulmonary tumor burden. The experiment was terminated at day 14 when the lungs of the control animals had sufficient tumor mass to provide meaningful evaluation. At that time, the lungs of all remaining animals were excised, weighed, and the number of tumor foci greater than 2 mm in diameter counted. The resulting data showed that both dosages of α (IV) NC1 hexamer significantly reduced the number of visible lung metastases (Mann-Whitney Rank Sum Test, $p<0.05$), with 8 visible lung metastases in the control, vs. 5 (100 μg/mouse) and 4 (200 μg/mouse), and the 100 μg/mouse dosage reduced the lung weights from a median of 520 mg in controls to a median of 462 mg in experimental, while the median lung weight of mice treated with 200 μg/mouse was 620 mg.

Other in vivo studies demonstrated that tumor cell metastasis to the lung can be reduced by 50% or more using intravenous injections of the Type IV collagen domains in murine B16 melanoma, human A375SM melanoma xenografts. Furthermore, injection of the NC1 hexamer also significantly reduced the number of lung tumors in separate Lewis Lung tumor studies.

We conclude from all of the above studies that angiogenesis, tumor growth and metastasis, and endothelial cell adhesion to the ECM, can be inhibited by isolated, recombinant domains of type IV collagen. The present invention is thus broadly applicable to a variety of uses which include inhibition of angiogenesis and treatment of diseases and conditions with accompanying undesired angiogenesis, such as solid and blood-borne tumors including but not limited to melanomas, carcinomas, sarcomas, rhabdomyosarcoma, retinoblastoma., Ewing sarcoma, neuroblastoma, osteosarcoma, and leukemia.

The invention is further applicable to treating non-tumorigenic diseases and conditions with accompanying undesired angiogenesis, including but not limited to diabetic retinopathy, rheumatoid arthritis, retinal neovascularization, choroidal neovascularization, macular degeneration., corneal neovascularization, retinopathy of prematurity., corneal graft rejection, neovascular glaucoma., retrolental fibroplasia, epidemic keratoconjunctivitis, Vitamin A deficiency, contact lens overwear, atopic keratitis, superior limbic keratitis, pterygium keratitis sicca, sogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi's sarcoma, Mooren ulcer, Terrien's marginal degeneration, marginal keratolysis, traum, systemic lupus, polyarteritis, Wegeners sarcoidosis, scleritis, Steven's Johnson disease, radial keratotomy, sickle cell anemia, sarcoid, pseudoxanthoma elasticum, Pagets disease, vein occlusion, artery occulsion, carotid obstructive disease, chronic uveitis, chronic vitritis, Lyme's disease, Eales disease, Bechets disease, myopia, optic pits, Stargarts disease, pars planitis, chronic retinal detachment, hyperviscosity syndromes, toxoplasmosis, post-laser complications, abnormal proliferation of fibrovascular tissue, hemangiomas, Osler-Weber-Rendu, acquired immune deficiency syndrome, ocular neovascular disease, osteoarthritis, chronic inflammation, Crohn's disease, ulceritive colitis, psoriasis., atherosclerosis, and pemphigoid. See U.S. Pat. No. 5,712,291)

The invention is also broadly applicable to methods for inhibiting tumor growth and metastasis, reduction of scar tissue formation, reduction of complications due to cell adhesion in organ transplants, and the inhibition of lymphocyte adhesion and mobility.

While the fundamental novel features of the invention have been shown and described, it will be understood that various omissions, substitutions, and changes in the form and details illustrated may be made by those skilled in the art without departing from the spirit of the invention. For example, various modifications, additions. and/or substitutions can be made to the type IV collagen cc monomer chains that would be encompassed by the invention. It is the intention, therefore, to be limited only as indicated by the scope of the following claims:

We claim:

1. A method for treating an angiogenesis-mediated disease or condition in a mammal, comprising administering to a mammal with an angiogenesis-mediated disease or condition an amount effective to inhibit angiogenesis of a polypeptide composition comprising an isolated α3 NC1 α chain monomer of type IV collagen.

2. The method of claim 1 wherein the angiogenesis-mediated disease or condition is selected from the group consisting of solid tumors, blood-borne tumors, diabetic retinopathy, rheumatoid arthritis, retinal neovascularization, choroidal neovascularization, macular degeneration, corneal neovascularization, retinopathy of prematurity, corneal graft rejection, neovascular glaucoma, retrolental fibroplasia, epidemic keratoconjunctivitis, Vitamin A deficiency, contact lens overwear, atopic keratitis, superior limbic keratitis, pterygium keratitis sicca, sogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi's sarcoma, Mooren ulcer, Terrien's marginal degeneration, marginal keratolysis, trauma, systemic lupus, polyarteritis, Wegeners sarcoidosis, scleritis, Steven's Johnson disease, radial keratotomy, sickle cell anemia, sarcoid, pseudoxanthoma elasticum, Pagets disease, vein occlusion, artery occulsion, carotid obstructive disease, chronic uveitis, chronic vitritis, Lyme's disease, Eales disease, Bechets disease, myopia, optic pits, Stargarts disease, pars planitis, chronic retinal detachment, hyperviscosity syndromes, toxoplasmosis, post-laser complications, abnormal proliferation of fibrovascular tissue, hemangiomas, Osler-Weber-Rendu, acquired immune deficiency syndrome, ocular neovascular disease, osteoarthritis, chronic inflammation, Crohn's disease, ulceritive colitis, psoriasis, atherosclerosis, and pemphigoid.

3. The method of claim 2 wherein the angiogenesis-mediated disease or condition is a solid tumor.

* * * * *

SEQUENCE LISTING

<160> NUMBER OF SEQ ID NOS: 12

<210> SEQ ID NO 1
<211> LENGTH: 900
<212> TYPE: DNA
<213> ORGANISM: Human
<220> FEATURE:
<221> NAME/KEY: CDS
<222> LOCATION: (40)..(819)

<400> SEQUENCE: 1

```
ctgccgcctg cctgcctgcc actgagggtt cccagcacc atg agg gcc tgg atc        54
                                            Met Arg Ala Trp Ile
                                            1               5 ttc ttt ctc ctt tgc ctg gcc ggg agg gct ctg gca gcc cca cta gcc      102
Phe Phe Leu Leu Cys Leu Ala Gly Arg Ala Leu Ala Ala Pro Leu Ala
            10                  15                  20 gac tac aag gac gac gat gac aag cta gca tct gtt gat cac ggc ttc      150
Asp Tyr Lys Asp Asp Asp Asp Lys Leu Ala Ser Val Asp His Gly Phe
        25                  30                  35 ctt gtg acc agg cat agt caa aca ata gat gac cca cag tgt cct tct      198
Leu Val Thr Arg His Ser Gln Thr Ile Asp Asp Pro Gln Cys Pro Ser
    40                  45                  50 ggg acc aaa att ctt tac cac ggg tac tct ttg ctc tac gtg caa ggc      246
Gly Thr Lys Ile Leu Tyr His Gly Tyr Ser Leu Leu Tyr Val Gln Gly
55                  60                  65 aat gaa cgg gcc cat ggc cag gac ttg ggc acg gcc ggc agc tgc ctg      294
Asn Glu Arg Ala His Gly Gln Asp Leu Gly Thr Ala Gly Ser Cys Leu
70                  75                  80                  85 cgc aag ttc agc aca atg ccc ttc ctg ttc tgc aat att aac aac gtg      342
Arg Lys Phe Ser Thr Met Pro Phe Leu Phe Cys Asn Ile Asn Asn Val
                90                  95                 100 tgc aac ttt gca tca cga aat gac tac tcg tac tgg ctg tcc acc cct      390
Cys Asn Phe Ala Ser Arg Asn Asp Tyr Ser Tyr Trp Leu Ser Thr Pro
            105                 110                 115 gag ccc atg ccc atg tca atg gca ccc atc acg ggg gaa aac ata aga      438
Glu Pro Met Pro Met Ser Met Ala Pro Ile Thr Gly Glu Asn Ile Arg
        120                 125                 130 cca ttt att agt agg tgt gct gtg tgt gag gcg cct gcc atg gtg atg      486
Pro Phe Ile Ser Arg Cys Ala Val Cys Glu Ala Pro Ala Met Val Met
    135                 140                 145 gcc gtg cac agc cag acc att cag atc cca ccg tgc ccc agc ggg tgg      534
Ala Val His Ser Gln Thr Ile Gln Ile Pro Pro Cys Pro Ser Gly Trp
```

```
                150                 155                 160                 165
tcc tcg ctg tgg atc ggc tac tct ttt gtg atg cac acc agc gct ggt        582
Ser Ser Leu Trp Ile Gly Tyr Ser Phe Val Met His Thr Ser Ala Gly
            170                 175                 180 gca gaa ggc tct ggc caa gcc ctg gcg tcc ccc ggc tcc tgc ctg gag        630
Ala Glu Gly Ser Gly Gln Ala Leu Ala Ser Pro Gly Ser Cys Leu Glu
                185                 190                 195 gag ttt aga agt gcg cca ttc atc gag tgt cac ggc cgt ggg acc tgc        678
Glu Phe Arg Ser Ala Pro Phe Ile Glu Cys His Gly Arg Gly Thr Cys
                200                 205                 210 aat tac tac gca aac gct tac agc ttt tgg ctc gcc acc ata gag agg        726
Asn Tyr Tyr Ala Asn Ala Tyr Ser Phe Trp Leu Ala Thr Ile Glu Arg
            215                 220                 225 agc gag atg ttc aag aag cct acg ccg tcc acc ttg aag gca ggg gag        774
Ser Glu Met Phe Lys Lys Pro Thr Pro Ser Thr Leu Lys Ala Gly Glu
230                 235                 240                 245 ctg cgc acg cac gtc agc cgc tgc caa gtc tgt atg aga aga aca            819
Leu Arg Thr His Val Ser Arg Cys Gln Val Cys Met Arg Arg Thr
                250                 255                 260 taatgaagcc tgactcagct accgcgggcc ctattctata gtgtcaccta aatgctagag      879
ctcgctgatc agcctcgact g                                                900

<210> SEQ ID NO 2
<211> LENGTH: 260
<212> TYPE: PRT
<213> ORGANISM: Human

<400> SEQUENCE: 2

Met Arg Ala Trp Ile Phe Phe Leu Leu Cys Leu Ala Gly Arg Ala Leu
1               5                   10                  15

Ala Ala Pro Leu Ala Asp Tyr Lys Asp Asp Asp Lys Leu Ala Ser
            20                  25                  30

Val Asp His Gly Phe Leu Val Thr Arg His Ser Gln Thr Ile Asp Asp
        35                  40                  45

Pro Gln Cys Pro Ser Gly Thr Lys Ile Leu Tyr His Gly Tyr Ser Leu
    50                  55                  60

Leu Tyr Val Gln Gly Asn Glu Arg Ala His Gly Gln Asp Leu Gly Thr
65                  70                  75                  80

Ala Gly Ser Cys Leu Arg Lys Phe Ser Thr Met Pro Phe Leu Phe Cys
                85                  90                  95

Asn Ile Asn Asn Val Cys Asn Phe Ala Ser Arg Asn Asp Tyr Ser Tyr
            100                 105                 110

Trp Leu Ser Thr Pro Glu Pro Met Pro Met Ser Met Ala Pro Ile Thr
        115                 120                 125

Gly Glu Asn Ile Arg Pro Phe Ile Ser Arg Cys Ala Val Cys Glu Ala
    130                 135                 140

Pro Ala Met Val Met Ala Val His Ser Gln Thr Ile Gln Ile Pro Pro
145                 150                 155                 160

Cys Pro Ser Gly Trp Ser Ser Leu Trp Ile Gly Tyr Ser Phe Val Met
                165                 170                 175

His Thr Ser Ala Gly Ala Glu Gly Ser Gly Gln Ala Leu Ala Ser Pro
            180                 185                 190

Gly Ser Cys Leu Glu Glu Phe Arg Ser Ala Pro Phe Ile Glu Cys His
        195                 200                 205

Gly Arg Gly Thr Cys Asn Tyr Tyr Ala Asn Ala Tyr Ser Phe Trp Leu
    210                 215                 220
```

-continued

```
Ala Thr Ile Glu Arg Ser Glu Met Phe Lys Lys Pro Thr Pro Ser Thr
225                 230                 235                 240

Leu Lys Ala Gly Glu Leu Arg Thr His Val Ser Arg Cys Gln Val Cys
            245                 250                 255

Met Arg Arg Thr
            260

<210> SEQ ID NO 3
<211> LENGTH: 900
<212> TYPE: DNA
<213> ORGANISM: Human
<220> FEATURE:
<221> NAME/KEY: CDS
<222> LOCATION: (40)..(813)

<400> SEQUENCE: 3
ctgccgcctg cctgcctgcc actgagggtt cccagcacc atg agg gcc tgg atc      54
                                           Met Arg Ala Trp Ile
                                             1               5 ttc ttt ctc ctt tgc ctg gcc ggg agg gct ctg gca gcc cca cta gcc    102
Phe Phe Leu Leu Cys Leu Ala Gly Arg Ala Leu Ala Ala Pro Leu Ala
             10                  15                  20 gac tac aag gac gac gat gac aag cta gcc gtc agc atc ggc tac ctc    150
Asp Tyr Lys Asp Asp Asp Asp Lys Leu Ala Val Ser Ile Gly Tyr Leu
         25                  30                  35 ctg gtg aag cac agc cag acg gac cag gag ccc atg tgc ccg gtg ggc    198
Leu Val Lys His Ser Gln Thr Asp Gln Glu Pro Met Cys Pro Val Gly
     40                  45                  50 atg aac aaa ctc tgg agt gga tac agc ctg ctg tac ttc gag ggc cag    246
Met Asn Lys Leu Trp Ser Gly Tyr Ser Leu Leu Tyr Phe Glu Gly Gln
 55                  60                  65 gag aag gcg cac aac cag gac ctg ggc ctg gcg ggc tcc tgc ctg gcg    294
Glu Lys Ala His Asn Gln Asp Leu Gly Leu Ala Gly Ser Cys Leu Ala
 70                  75                  80                  85 cgg ttc agc acc atg ccc ttc ctg tac tgc aac cct ggt gat gtc tgc    342
Arg Phe Ser Thr Met Pro Phe Leu Tyr Cys Asn Pro Gly Asp Val Cys
                 90                  95                 100 tac tat gcc agc cgg aac gac aag tcc tac tgg ctc tct acc act gcg    390
Tyr Tyr Ala Ser Arg Asn Asp Lys Ser Tyr Trp Leu Ser Thr Thr Ala
            105                 110                 115 ccg ctg ccc atg atg ccc gtg gcc gag gac gag atc aag ccc tac atc    438
Pro Leu Pro Met Met Pro Val Ala Glu Asp Glu Ile Lys Pro Tyr Ile
        120                 125                 130 agc cgc tgt tct gtg tgt gag gcc ccg gcc atc gcc atc gcg gtc cac    486
Ser Arg Cys Ser Val Cys Glu Ala Pro Ala Ile Ala Ile Ala Val His
    135                 140                 145 agt cag gat gtc tcc atc cca cac tgc cca gct ggg tgg cgg agt ttg    534
Ser Gln Asp Val Ser Ile Pro His Cys Pro Ala Gly Trp Arg Ser Leu
150                 155                 160                 165 tgg atc gga tat tcc ttc ctc atg cac acg gcg gcg gga gac gaa ggc    582
Trp Ile Gly Tyr Ser Phe Leu Met His Thr Ala Ala Gly Asp Glu Gly
                170                 175                 180 ggt ggc caa tca ctg gtg tca ccg ggc agc tgt cta gag gac ttc cgc    630
Gly Gly Gln Ser Leu Val Ser Pro Gly Ser Cys Leu Glu Asp Phe Arg
            185                 190                 195 gcc aca cca ttc atc gaa tgc aat gga ggc cgc ggc acc tgc cac tac    678
Ala Thr Pro Phe Ile Glu Cys Asn Gly Gly Arg Gly Thr Cys His Tyr
        200                 205                 210 tac gcc aac aag tac agc ttc tgg ctg acc acc att ccc gag cag agc    726
Tyr Ala Asn Lys Tyr Ser Phe Trp Leu Thr Thr Ile Pro Glu Gln Ser
```

```
                215                 220                 225
ttc cag ggc tcg ccc tcc gcc gac acg ctc aag gcc ggc ctc atc cgc    774
Phe Gln Gly Ser Pro Ser Ala Asp Thr Leu Lys Ala Gly Leu Ile Arg
230                 235                 240                 245 aca cac atc agc cgc tgc cag gtg tgc atg aag aac ctg tgagccggcg     823
Thr His Ile Ser Arg Cys Gln Val Cys Met Lys Asn Leu
                250                 255 cgtgccaggg ccctattcta tagtgtcacc taaatgctag agctcgctga tcagcctcga  883
ctgtgccttc tagttgc                                                 900

<210> SEQ ID NO 4
<211> LENGTH: 258
<212> TYPE: PRT
<213> ORGANISM: Human

<400> SEQUENCE: 4

Met Arg Ala Trp Ile Phe Phe Leu Leu Cys Leu Ala Gly Arg Ala Leu
1               5                   10                  15

Ala Ala Pro Leu Ala Asp Tyr Lys Asp Asp Asp Lys Leu Ala Val
            20                  25                  30

Ser Ile Gly Tyr Leu Leu Val Lys His Ser Gln Thr Asp Gln Glu Pro
        35                  40                  45

Met Cys Pro Val Gly Met Asn Lys Leu Trp Ser Gly Tyr Ser Leu Leu
    50                  55                  60

Tyr Phe Glu Gly Gln Glu Lys Ala His Asn Gln Asp Leu Gly Leu Ala
65                  70                  75                  80

Gly Ser Cys Leu Ala Arg Phe Ser Thr Met Pro Phe Leu Tyr Cys Asn
                85                  90                  95

Pro Gly Asp Val Cys Tyr Tyr Ala Ser Arg Asn Asp Lys Ser Tyr Trp
            100                 105                 110

Leu Ser Thr Thr Ala Pro Leu Pro Met Met Pro Val Ala Glu Asp Glu
        115                 120                 125

Ile Lys Pro Tyr Ile Ser Arg Cys Ser Val Cys Glu Ala Pro Ala Ile
    130                 135                 140

Ala Ile Ala Val His Ser Gln Asp Val Ser Ile Pro His Cys Pro Ala
145                 150                 155                 160

Gly Trp Arg Ser Leu Trp Ile Gly Tyr Ser Phe Leu Met His Thr Ala
                165                 170                 175

Ala Gly Asp Glu Gly Gly Gly Gln Ser Leu Val Ser Pro Gly Ser Cys
            180                 185                 190

Leu Glu Asp Phe Arg Ala Thr Pro Phe Ile Glu Cys Asn Gly Gly Arg
        195                 200                 205

Gly Thr Cys His Tyr Tyr Ala Asn Lys Tyr Ser Phe Trp Leu Thr Thr
    210                 215                 220

Ile Pro Glu Gln Ser Phe Gln Gly Ser Pro Ser Ala Asp Thr Leu Lys
225                 230                 235                 240

Ala Gly Leu Ile Arg Thr His Ile Ser Arg Cys Gln Val Cys Met Lys
                245                 250                 255

Asn Leu

<210> SEQ ID NO 5
<211> LENGTH: 900
<212> TYPE: DNA
<213> ORGANISM: Human
<220> FEATURE:
<221> NAME/KEY: CDS
```

<222> LOCATION: (40)..(843)

<400> SEQUENCE: 5

```
ctgccgcctg cctgcctgcc actgagggtt cccagcacc atg agg gcc tgg atc         54
                                            Met Arg Ala Trp Ile
                                              1               5 ttc ttt ctc ctt tgc ctg gcc ggg agg gct ctg gca gcc ccg cta gcc        102
Phe Phe Leu Leu Cys Leu Ala Gly Arg Ala Leu Ala Ala Pro Leu Ala
             10                  15                  20 gac tac aag gac gac gat gac aaa cgt gga gac agt gga tca cct gca        150
Asp Tyr Lys Asp Asp Asp Asp Lys Arg Gly Asp Ser Gly Ser Pro Ala
         25                  30                  35 acc tgg aca acg aga ggc ttt gtc ttc acc cga cac agt caa acc aca        198
Thr Trp Thr Thr Arg Gly Phe Val Phe Thr Arg His Ser Gln Thr Thr
     40                  45                  50 gca att cct tca tgt cca gag ggg aca gtg cca ctc tac agt ggg ttt        246
Ala Ile Pro Ser Cys Pro Glu Gly Thr Val Pro Leu Tyr Ser Gly Phe
 55                  60                  65 tct ttt ctt ttt gta caa gga aat caa cga gcc cac gga caa gac ctt        294
Ser Phe Leu Phe Val Gln Gly Asn Gln Arg Ala His Gly Gln Asp Leu
 70                  75                  80                  85 gga act ctt ggc agc tgc ctg cag cga ttt acc aca atg cca ttc tta        342
Gly Thr Leu Gly Ser Cys Leu Gln Arg Phe Thr Thr Met Pro Phe Leu
                 90                  95                 100 ttc tgc aat gtc aat gat gta tgt aat ttt gca tct cga aat gat tat        390
Phe Cys Asn Val Asn Asp Val Cys Asn Phe Ala Ser Arg Asn Asp Tyr
            105                 110                 115 tca tac tgg ctg tca aca cca gct ctg atg cca atg aac atg gct ccc        438
Ser Tyr Trp Leu Ser Thr Pro Ala Leu Met Pro Met Asn Met Ala Pro
        120                 125                 130 att act ggc aga gcc ctt gag cct tat ata agc aga tgc act gtt tgt        486
Ile Thr Gly Arg Ala Leu Glu Pro Tyr Ile Ser Arg Cys Thr Val Cys
    135                 140                 145 gaa ggt cct gcg atc gcc ata gcc gtt cac agc caa acc act gac att        534
Glu Gly Pro Ala Ile Ala Ile Ala Val His Ser Gln Thr Thr Asp Ile
150                 155                 160                 165 cct cca tgt cct cac ggc tgg att tct ctc tgg aaa gga ttt tca ttc        582
Pro Pro Cys Pro His Gly Trp Ile Ser Leu Trp Lys Gly Phe Ser Phe
                170                 175                 180 atc atg ttc aca agt gca ggt tct gag ggc gcc ggg caa gca ctg gcc        630
Ile Met Phe Thr Ser Ala Gly Ser Glu Gly Ala Gly Gln Ala Leu Ala
            185                 190                 195 tcc ccc ggc tcc tgc ctg gaa gaa ttc cga gcc agc cca ttt cta gaa        678
Ser Pro Gly Ser Cys Leu Glu Glu Phe Arg Ala Ser Pro Phe Leu Glu
        200                 205                 210 tgt cat gga aga gga acg tgc aac tac tat tca aat tcc tac agt ttc        726
Cys His Gly Arg Gly Thr Cys Asn Tyr Tyr Ser Asn Ser Tyr Ser Phe
    215                 220                 225 tgg ctg gct tca tta aac cca gaa aga atg ttc aga aag cct att cca        774
Trp Leu Ala Ser Leu Asn Pro Glu Arg Met Phe Arg Lys Pro Ile Pro
230                 235                 240                 245 tca act gtg aaa gct ggg gaa tta gaa aaa ata ata agt cgc tgt cag        822
Ser Thr Val Lys Ala Gly Glu Leu Glu Lys Ile Ile Ser Arg Cys Gln
                250                 255                 260 gtg tgc atg aag aaa aga cac tgagggccct attctatagt gtcacctaaa          873
Val Cys Met Lys Lys Arg His
                265 tgctagagct cgctgatcag cctcgac                                         900
```

<210> SEQ ID NO 6
<211> LENGTH: 268
<212> TYPE: PRT
<213> ORGANISM: Human

<400> SEQUENCE: 6

Met Arg Ala Trp Ile Phe Phe Leu Leu Cys Leu Ala Gly Arg Ala Leu
 1               5                  10                  15

Ala Ala Pro Leu Ala Asp Tyr Lys Asp Asp Asp Lys Arg Gly Asp
             20                  25                  30

Ser Gly Ser Pro Ala Thr Trp Thr Thr Arg Gly Phe Val Phe Thr Arg
         35                  40                  45

His Ser Gln Thr Thr Ala Ile Pro Ser Cys Pro Glu Gly Thr Val Pro
     50                  55                  60

Leu Tyr Ser Gly Phe Ser Phe Leu Phe Val Gln Gly Asn Gln Arg Ala
 65                  70                  75                  80

His Gly Gln Asp Leu Gly Thr Leu Gly Ser Cys Leu Gln Arg Phe Thr
                 85                  90                  95

Thr Met Pro Phe Leu Phe Cys Asn Val Asn Asp Val Cys Asn Phe Ala
            100                 105                 110

Ser Arg Asn Asp Tyr Ser Tyr Trp Leu Ser Thr Pro Ala Leu Met Pro
        115                 120                 125

Met Asn Met Ala Pro Ile Thr Gly Arg Ala Leu Glu Pro Tyr Ile Ser
130                 135                 140

Arg Cys Thr Val Cys Glu Gly Pro Ala Ile Ala Ile Ala Val His Ser
145                 150                 155                 160

Gln Thr Thr Asp Ile Pro Pro Cys Pro His Gly Trp Ile Ser Leu Trp
                165                 170                 175

Lys Gly Phe Ser Phe Ile Met Phe Thr Ser Ala Gly Ser Glu Gly Ala
            180                 185                 190

Gly Gln Ala Leu Ala Ser Pro Gly Ser Cys Leu Glu Glu Phe Arg Ala
        195                 200                 205

Ser Pro Phe Leu Glu Cys His Gly Arg Gly Thr Cys Asn Tyr Tyr Ser
    210                 215                 220

Asn Ser Tyr Ser Phe Trp Leu Ala Ser Leu Asn Pro Glu Arg Met Phe
225                 230                 235                 240

Arg Lys Pro Ile Pro Ser Thr Val Lys Ala Gly Glu Leu Glu Lys Ile
                245                 250                 255

Ile Ser Arg Cys Gln Val Cys Met Lys Lys Arg His
            260                 265

<210> SEQ ID NO 7
<211> LENGTH: 900
<212> TYPE: DNA
<213> ORGANISM: Human
<220> FEATURE:
<221> NAME/KEY: CDS
<222> LOCATION: (40)..(819)

<400> SEQUENCE: 7
ctgccgcctg cctgcctgcc actgagggtt cccagcacc atg agg gcc tgg atc        54
                                           Met Arg Ala Trp Ile
                                            1               5 ttc ttt ctc ctt tgc ctg gcc ggg agg gct ctg gca gcc ccg cta gcc     102
Phe Phe Leu Leu Cys Leu Ala Gly Arg Ala Leu Ala Ala Pro Leu Ala
                 10                  15                  20 gac tac aag gac gac gat gac aag cct gga tac ctc ggt ggc ttc ctc     150
Asp Tyr Lys Asp Asp Asp Asp Lys Pro Gly Tyr Leu Gly Gly Phe Leu

|  |  |  |  |  |  |  |  |  |  |  |  |  |  |  |  |
|---|---|---|---|---|---|---|---|---|---|---|---|---|---|---|---|
|  |  |  | 25 |  |  |  |  | 30 |  |  |  |  | 35 |  |  |
| ctg | gtt | ctc | cac | agt | cag | acg | gac | cag | gag | ccc | acc | tgc | ccc | ctg | ggc | 198 |
| Leu | Val | Leu | His | Ser | Gln | Thr | Asp | Gln | Glu | Pro | Thr | Cys | Pro | Leu | Gly |  |
|  |  |  | 40 |  |  |  |  | 45 |  |  |  |  | 50 |  |  |
| atg | ccc | agg | ctc | tgg | act | ggg | tat | agt | ctg | tta | tac | ctg | gaa | ggg | caa | 246 |
| Met | Pro | Arg | Leu | Trp | Thr | Gly | Tyr | Ser | Leu | Leu | Tyr | Leu | Glu | Gly | Gln |  |
|  |  |  | 55 |  |  |  |  | 60 |  |  |  |  | 65 |  |  |
| gag | aaa | gct | cac | aat | caa | gac | ctt | ggt | ctg | gca | ggg | tct | tgc | ctt | ccc | 294 |
| Glu | Lys | Ala | His | Asn | Gln | Asp | Leu | Gly | Leu | Ala | Gly | Ser | Cys | Leu | Pro |  |
|  |  |  | 70 |  |  |  |  | 75 |  |  |  |  | 80 |  | 85 |
| gta | ttt | agc | acg | ctg | ccc | ttt | gcc | tac | tgc | aac | atc | cac | cag | gtg | tgc | 342 |
| Val | Phe | Ser | Thr | Leu | Pro | Phe | Ala | Tyr | Cys | Asn | Ile | His | Gln | Val | Cys |  |
|  |  |  |  |  | 90 |  |  |  |  | 95 |  |  |  |  | 100 |
| cac | tat | gcc | cag | aga | aac | gac | aga | tcc | tac | tgg | ctg | gcc | agc | gct | gcg | 390 |
| His | Tyr | Ala | Gln | Arg | Asn | Asp | Arg | Ser | Tyr | Trp | Leu | Ala | Ser | Ala | Ala |  |
|  |  |  |  | 105 |  |  |  |  | 110 |  |  |  |  | 115 |  |
| ccc | ctc | ccc | atg | atg | cca | ctc | tct | gaa | gag | gcg | atc | cgc | ccc | tat | gtc | 438 |
| Pro | Leu | Pro | Met | Met | Pro | Leu | Ser | Glu | Glu | Ala | Ile | Arg | Pro | Tyr | Val |  |
|  |  | 120 |  |  |  |  | 125 |  |  |  |  | 130 |  |  |  |
| agc | cgc | tgt | gcg | gta | tgc | gag | gcc | ccg | gcc | cag | gcg | gtg | gcg | gtg | cac | 486 |
| Ser | Arg | Cys | Ala | Val | Cys | Glu | Ala | Pro | Ala | Gln | Ala | Val | Ala | Val | His |  |
| 135 |  |  |  | 140 |  |  |  |  | 145 |  |  |  |  |  |  |
| agc | cag | gac | cag | tcc | atc | ccc | cca | tgt | ccg | cag | acc | tgg | agg | agc | ctc | 534 |
| Ser | Gln | Asp | Gln | Ser | Ile | Pro | Pro | Cys | Pro | Gln | Thr | Trp | Arg | Ser | Leu |  |
| 150 |  |  |  | 155 |  |  |  |  | 160 |  |  |  |  | 165 |  |
| tgg | atc | ggg | tat | tca | ttc | ctg | atg | cac | aca | gga | gct | ggg | gac | caa | gga | 582 |
| Trp | Ile | Gly | Tyr | Ser | Phe | Leu | Met | His | Thr | Gly | Ala | Gly | Asp | Gln | Gly |  |
|  |  |  | 170 |  |  |  |  | 175 |  |  |  |  | 180 |  |  |
| gga | ggg | cag | gcc | ctt | atg | tca | cct | ggc | agc | tgc | ctg | gaa | gat | ttc | aga | 630 |
| Gly | Gly | Gln | Ala | Leu | Met | Ser | Pro | Gly | Ser | Cys | Leu | Glu | Asp | Phe | Arg |  |
|  |  |  | 185 |  |  |  |  | 190 |  |  |  |  | 195 |  |  |
| gca | gca | cca | ttc | ctt | gaa | tgc | agg | gcc | cgg | cag | gga | act | tgc | cac | ttt | 678 |
| Ala | Ala | Pro | Phe | Leu | Glu | Cys | Gln | Gly | Arg | Gln | Gly | Thr | Cys | His | Phe |  |
|  |  | 200 |  |  |  |  | 205 |  |  |  |  | 210 |  |  |  |
| ttc | gca | aat | aag | tat | agc | ttc | tgg | ctc | aca | acg | gtg | aaa | gca | gac | ttg | 726 |
| Phe | Ala | Asn | Lys | Tyr | Ser | Phe | Trp | Leu | Thr | Thr | Val | Lys | Ala | Asp | Leu |  |
|  | 215 |  |  |  |  | 220 |  |  |  |  | 225 |  |  |  |  |
| cag | ttt | tcc | tct | gct | cca | gca | cca | gac | acc | tta | aaa | gaa | agc | cag | gcc | 774 |
| Gln | Phe | Ser | Ser | Ala | Pro | Ala | Pro | Asp | Thr | Leu | Lys | Glu | Ser | Gln | Ala |
| 230 |  |  |  | 235 |  |  |  |  | 240 |  |  |  |  | 245 |  |
| caa | cgc | cag | aaa | atc | agc | cgg | tgc | cag | gtc | tgc | gtg | aag | tat | agc |  | 819 |
| Gln | Arg | Gln | Lys | Ile | Ser | Arg | Cys | Gln | Val | Cys | Val | Lys | Tyr | Ser |  |  |
|  |  |  | 250 |  |  |  |  | 255 |  |  |  |  | 260 |  |  | tagggccct attctatagt gtcacctaaa tgctagagct cgctgatcag cctcgactgt   879 gccttctagt tgccagccat c   900

<210> SEQ ID NO 8
<211> LENGTH: 260
<212> TYPE: PRT
<213> ORGANISM: Human

<400> SEQUENCE: 8

Met Arg Ala Trp Ile Phe Phe Leu Leu Cys Leu Ala Gly Arg Ala Leu
 1               5                   10                  15

Ala Ala Pro Leu Ala Asp Tyr Lys Asp Asp Asp Lys Pro Gly Tyr
            20                  25                  30

Leu Gly Gly Phe Leu Leu Val Leu His Ser Gln Thr Asp Gln Glu Pro
        35                  40                  45

-continued

```
Thr Cys Pro Leu Gly Met Pro Arg Leu Trp Thr Gly Tyr Ser Leu Leu
         50                  55                  60

Tyr Leu Glu Gly Gln Glu Lys Ala His Asn Gln Asp Leu Gly Leu Ala
 65                  70                  75                  80

Gly Ser Cys Leu Pro Val Phe Ser Thr Leu Pro Phe Ala Tyr Cys Asn
                 85                  90                  95

Ile His Gln Val Cys His Tyr Ala Gln Arg Asn Asp Arg Ser Tyr Trp
                100                 105                 110

Leu Ala Ser Ala Ala Pro Leu Pro Met Met Pro Leu Ser Glu Glu Ala
            115                 120                 125

Ile Arg Pro Tyr Val Ser Arg Cys Ala Val Cys Glu Ala Pro Ala Gln
        130                 135                 140

Ala Val Ala Val His Ser Gln Asp Gln Ser Ile Pro Pro Cys Pro Gln
145                 150                 155                 160

Thr Trp Arg Ser Leu Trp Ile Gly Tyr Ser Phe Leu Met His Thr Gly
                165                 170                 175

Ala Gly Asp Gln Gly Gly Gln Ala Leu Met Ser Pro Gly Ser Cys
            180                 185                 190

Leu Glu Asp Phe Arg Ala Ala Pro Phe Leu Glu Cys Gln Gly Arg Gln
        195                 200                 205

Gly Thr Cys His Phe Phe Ala Asn Lys Tyr Ser Phe Trp Leu Thr Thr
    210                 215                 220

Val Lys Ala Asp Leu Gln Phe Ser Ser Ala Pro Ala Asp Thr Leu
225                 230                 235                 240

Lys Glu Ser Gln Ala Gln Arg Gln Lys Ile Ser Arg Cys Gln Val Cys
                245                 250                 255

Val Lys Tyr Ser
            260

<210> SEQ ID NO 9
<211> LENGTH: 900
<212> TYPE: DNA
<213> ORGANISM: Human
<220> FEATURE:
<221> NAME/KEY: CDS
<222> LOCATION: (40)..(831)

<400> SEQUENCE: 9
ctgccgcctg cctgcctgcc actgagggtt cccagcacc atg agg gcc tgg atc         54
                                            Met Arg Ala Trp Ile
                                              1               5 ttc ttt ctc ctt tgc ctg gcc ggg agg gct ctg gca gcc ccg cta gct      102
Phe Phe Leu Leu Cys Leu Ala Gly Arg Ala Leu Ala Ala Pro Leu Ala
                10                  15                  20 gac tac aag gac gac gat gac aaa ggt ccc cct gga acc tcc tct gtt      150
Asp Tyr Lys Asp Asp Asp Asp Lys Gly Pro Pro Gly Thr Ser Ser Val
            25                  30                  35 gca cat gga ttt ctt att aca cgc cac agc cag aca acg gat gca cca      198
Ala His Gly Phe Leu Ile Thr Arg His Ser Gln Thr Thr Asp Ala Pro
        40                  45                  50 caa tgc cca cag gga aca ctt cag gtc tat gaa ggc ttt tct ctc ctg      246
Gln Cys Pro Gln Gly Thr Leu Gln Val Tyr Glu Gly Phe Ser Leu Leu
    55                  60                  65 tat gta caa gga aat aaa aga gcc cac ggt caa gac ttg ggg acg gct      294
Tyr Val Gln Gly Asn Lys Arg Ala His Gly Gln Asp Leu Gly Thr Ala
 70                  75                  80                  85 ggc agc tgc ctt cgt cgc ttt agt acc atg cct ttc atg ttc tgc aac      342
Gly Ser Cys Leu Arg Arg Phe Ser Thr Met Pro Phe Met Phe Cys Asn
```

```
                  90              95              100
atc aat aat gtt tgc aac ttt gct tca aga aat gac tat tct tac tgg      390
Ile Asn Asn Val Cys Asn Phe Ala Ser Arg Asn Asp Tyr Ser Tyr Trp
            105             110             115 ctc tct acc cca gag ccc atg cca atg agc atg caa ccc cta aag ggc      438
Leu Ser Thr Pro Glu Pro Met Pro Met Ser Met Gln Pro Leu Lys Gly
        120             125             130 cag agc atc cag cca ttc att agt cga tgt gca gta tgt gaa gct cca      486
Gln Ser Ile Gln Pro Phe Ile Ser Arg Cys Ala Val Cys Glu Ala Pro
    135             140             145 gct gtg gtg atc gca gtt cac agt cag acg atc cag att ccc cat tgt      534
Ala Val Val Ile Ala Val His Ser Gln Thr Ile Gln Ile Pro His Cys
150             155             160             165 cct cag gga tgg gat tct ctg tgg att ggt tat tcc ttc atg atg cat      582
Pro Gln Gly Trp Asp Ser Leu Trp Ile Gly Tyr Ser Phe Met Met His
            170             175             180 aca agt gca ggg gca gaa ggc tca ggt caa gcc cta gcc tcc cct ggt      630
Thr Ser Ala Gly Ala Glu Gly Ser Gly Gln Ala Leu Ala Ser Pro Gly
        185             190             195 tcc tgc ttg gaa gag ttt cgt tca gct ccc ttc atc gaa tgt cat ggg      678
Ser Cys Leu Glu Glu Phe Arg Ser Ala Pro Phe Ile Glu Cys His Gly
    200             205             210 agg ggt acc tgt aac tac tat gcc aac tcc tac agc ttt tgg ctg gca      726
Arg Gly Thr Cys Asn Tyr Tyr Ala Asn Ser Tyr Ser Phe Trp Leu Ala
215             220             225 act gta gat gtg tca gac atg ttc agt aaa cct cag tca gaa acg ctg      774
Thr Val Asp Val Ser Asp Met Phe Ser Lys Pro Gln Ser Glu Thr Leu
            230             235             240             245 aaa gca gga gac ttg agg aca cga att agc cga tgt caa gtg tgc atg      822
Lys Ala Gly Asp Leu Arg Thr Arg Ile Ser Arg Cys Gln Val Cys Met
        250             255             260 aag agg aca taacgcggcc gctcgagcat gcatctagag ggccctattc              871
Lys Arg Thr tatagtgtca cctaaatgct agagctcgc                                      900

<210> SEQ ID NO 10
<211> LENGTH: 264
<212> TYPE: PRT
<213> ORGANISM: Human

<400> SEQUENCE: 10

Met Arg Ala Trp Ile Phe Phe Leu Leu Cys Leu Ala Gly Arg Ala Leu
 1               5                  10                  15

Ala Ala Pro Leu Ala Asp Tyr Lys Asp Asp Asp Lys Gly Pro Pro
            20                  25                  30

Gly Thr Ser Ser Val Ala His Gly Phe Leu Ile Thr Arg His Ser Gln
            35                  40                  45

Thr Thr Asp Ala Pro Gln Cys Pro Gln Gly Thr Leu Gln Val Tyr Glu
    50                  55                  60

Gly Phe Ser Leu Leu Tyr Val Gln Gly Asn Lys Arg Ala His Gly Gln
65                  70                  75                  80

Asp Leu Gly Thr Ala Gly Ser Cys Leu Arg Arg Phe Ser Thr Met Pro
                85                  90                  95

Phe Met Phe Cys Asn Ile Asn Asn Val Cys Asn Phe Ala Ser Arg Asn
            100                 105                 110

Asp Tyr Ser Tyr Trp Leu Ser Thr Pro Glu Pro Met Pro Met Ser Met
        115                 120                 125
```

-continued

```
Gln Pro Leu Lys Gly Gln Ser Ile Gln Pro Phe Ile Ser Arg Cys Ala
    130                 135                 140

Val Cys Glu Ala Pro Ala Val Ile Ala Val His Ser Gln Thr Ile
145                 150                 155                 160

Gln Ile Pro His Cys Pro Gln Gly Trp Asp Ser Leu Trp Ile Gly Tyr
                165                 170                 175

Ser Phe Met Met His Thr Ser Ala Gly Ala Glu Gly Ser Gly Gln Ala
            180                 185                 190

Leu Ala Ser Pro Gly Ser Cys Leu Glu Glu Phe Arg Ser Ala Pro Phe
        195                 200                 205

Ile Glu Cys His Gly Arg Gly Thr Cys Asn Tyr Tyr Ala Asn Ser Tyr
    210                 215                 220

Ser Phe Trp Leu Ala Thr Val Asp Val Ser Asp Met Phe Ser Lys Pro
225                 230                 235                 240

Gln Ser Glu Thr Leu Lys Ala Gly Asp Leu Arg Thr Arg Ile Ser Arg
                245                 250                 255

Cys Gln Val Cys Met Lys Arg Thr
            260
```

<210> SEQ ID NO 11
<211> LENGTH: 900
<212> TYPE: DNA
<213> ORGANISM: Human
<220> FEATURE:
<221> NAME/KEY: CDS
<222> LOCATION: (40)..(819)

<400> SEQUENCE: 11

```
ctgccgcctg cctgcctgcc actgagggtt cccagcacc atg agg gcc tgg atc         54
                                          Met Arg Ala Trp Ile
                                            1               5 ttc ttt ctc ctt tgc ctg gcc ggg agg gct ctg gca gcc cca cta gcc       102
Phe Phe Leu Leu Cys Leu Ala Gly Arg Ala Leu Ala Ala Pro Leu Ala
                 10                  15                  20 gac tac aag gac gac gat gac aag cta gcg agc atg aga gtg ggc tac       150
Asp Tyr Lys Asp Asp Asp Asp Lys Leu Ala Ser Met Arg Val Gly Tyr
             25                  30                  35 acg ttg gta aag cac agc cag tcg gaa cag gtg ccc ccg tgt ccc atc       198
Thr Leu Val Lys His Ser Gln Ser Glu Gln Val Pro Pro Cys Pro Ile
         40                  45                  50 ggg atg agc cag ctg tgg gtg ggg tac agc tta ctg ttt gtg gag ggg       246
Gly Met Ser Gln Leu Trp Val Gly Tyr Ser Leu Leu Phe Val Glu Gly
     55                  60                  65 caa gag aaa gcc cac aac cag gac ctg ggc ttt gct ggc tcc tgt ctg       294
Gln Glu Lys Ala His Asn Gln Asp Leu Gly Phe Ala Gly Ser Cys Leu
 70                  75                  80                  85 ccc cgc ttc agc acc atg ccc ttc atc tac tgc aac atc aac gag gtg       342
Pro Arg Phe Ser Thr Met Pro Phe Ile Tyr Cys Asn Ile Asn Glu Val
                 90                  95                 100 tgc cac tat gcc agg cgc aat gat aaa tct tac tgg ctc tcc act acc       390
Cys His Tyr Ala Arg Arg Asn Asp Lys Ser Tyr Trp Leu Ser Thr Thr
            105                 110                 115 gcc cct atc ccc atg atg ccc gtc agc cag acc cag att ccc cag tac       438
Ala Pro Ile Pro Met Met Pro Val Ser Gln Thr Gln Ile Pro Gln Tyr
        120                 125                 130 atc agc cgc tgc tct gtg tgt gag gca ccc tcg caa gcc att gct gtg       486
Ile Ser Arg Cys Ser Val Cys Glu Ala Pro Ser Gln Ala Ile Ala Val
    135                 140                 145 cac agc cag gac atc acc atc ccg cag tgc ccc ctg ggc tgg cgc agc       534
```

```
His Ser Gln Asp Ile Thr Ile Pro Gln Cys Pro Leu Gly Trp Arg Ser
150                 155                 160                 165 ctc tgg att ggg tac tct ttc ctc atg cac act gcc gct ggt gcc gag    582
Leu Trp Ile Gly Tyr Ser Phe Leu Met His Thr Ala Ala Gly Ala Glu
                170                 175                 180 ggt gga ggc cag tcc ctg gtc tca cct ggc tcc tgc cta gag gac ttt    630
Gly Gly Gly Gln Ser Leu Val Ser Pro Gly Ser Cys Leu Glu Asp Phe
            185                 190                 195 cgg gcc act cct ttc atc gaa tgc agt ggt gcc cga ggc acc tgc cac    678
Arg Ala Thr Pro Phe Ile Glu Cys Ser Gly Ala Arg Gly Thr Cys His
        200                 205                 210 tac ttt gca aac aag tac agt ttc tgg ttg acc aca gtg gag gag agg    726
Tyr Phe Ala Asn Lys Tyr Ser Phe Trp Leu Thr Thr Val Glu Glu Arg
    215                 220                 225 cag cag ttt ggg gag ttg cct gtg tct gaa acg ctg aaa gct ggg cag    774
Gln Gln Phe Gly Glu Leu Pro Val Ser Glu Thr Leu Lys Ala Gly Gln
230                 235                 240                 245 ctc cac act cga gtc agt cgc tgc cag gtg tgt atg aaa agc ctg        819
Leu His Thr Arg Val Ser Arg Cys Gln Val Cys Met Lys Ser Leu
                250                 255                 260 tagggtggca cctgccacgg gccctattct atagtgtcac ctaaatgcta gagctcgctg    879
atcagcctcg actgtgcctt c                                              900

<210> SEQ ID NO 12
<211> LENGTH: 260
<212> TYPE: PRT
<213> ORGANISM: Human

<400> SEQUENCE: 12

Met Arg Ala Trp Ile Phe Phe Leu Leu Cys Leu Ala Gly Arg Ala Leu
1               5                   10                  15

Ala Ala Pro Leu Ala Asp Tyr Lys Asp Asp Asp Lys Leu Ala Ser
            20                  25                  30

Met Arg Val Gly Tyr Thr Leu Val Lys His Ser Gln Ser Glu Gln Val
        35                  40                  45

Pro Pro Cys Pro Ile Gly Met Ser Gln Leu Trp Val Gly Tyr Ser Leu
    50                  55                  60

Leu Phe Val Glu Gly Gln Glu Lys Ala His Asn Gln Asp Leu Gly Phe
65                  70                  75                  80

Ala Gly Ser Cys Leu Pro Arg Phe Ser Thr Met Pro Phe Ile Tyr Cys
                85                  90                  95

Asn Ile Asn Glu Val Cys His Tyr Ala Arg Arg Asn Asp Lys Ser Tyr
            100                 105                 110

Trp Leu Ser Thr Thr Ala Pro Ile Pro Met Met Pro Val Ser Gln Thr
        115                 120                 125

Gln Ile Pro Gln Tyr Ile Ser Arg Cys Ser Val Cys Glu Ala Pro Ser
    130                 135                 140

Gln Ala Ile Ala Val His Ser Gln Asp Ile Thr Ile Pro Gln Cys Pro
145                 150                 155                 160

Leu Gly Trp Arg Ser Leu Trp Ile Gly Tyr Ser Phe Leu Met His Thr
                165                 170                 175

Ala Ala Gly Ala Glu Gly Gly Gly Gln Ser Leu Val Ser Pro Gly Ser
            180                 185                 190

Cys Leu Glu Asp Phe Arg Ala Thr Pro Phe Ile Glu Cys Ser Gly Ala
        195                 200                 205

Arg Gly Thr Cys His Tyr Phe Ala Asn Lys Tyr Ser Phe Trp Leu Thr
```

```
               210                 215                 220
Thr Val Glu Glu Arg Gln Gln Phe Gly Glu Leu Pro Val Ser Glu Thr
225                 230                 235                 240

Leu Lys Ala Gly Gln Leu His Thr Arg Val Ser Arg Cys Gln Val Cys
                245                 250                 255

Met Lys Ser Leu
            260
```